US009139565B2

(12) United States Patent
Oyelere et al.

(10) Patent No.: US 9,139,565 B2
(45) Date of Patent: Sep. 22, 2015

(54) HISTONE DEACETYLASE (HDAC) INHIBITORS TARGETING PROSTATE TUMORS AND METHODS OF MAKING AND USING THEREOF

(75) Inventors: Adegboyega Oyelere, Marietta, GA (US); Berkley Gryder, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 44 days.

(21) Appl. No.: 13/824,661

(22) PCT Filed: Sep. 28, 2011

(86) PCT No.: PCT/US2011/053623
§ 371 (c)(1), (2), (4) Date: Jul. 3, 2013

(87) PCT Pub. No.: WO2012/050868
PCT Pub. Date: Apr. 19, 2012

(65) Prior Publication Data

US 2013/0289085 A1 Oct. 31, 2013

Related U.S. Application Data

(60) Provisional application No. 61/387,183, filed on Sep. 28, 2010.

(51) Int. Cl.

| | |
|---|---|
| ***C07D 233/02*** | (2006.01) |
| ***C07D 403/06*** | (2006.01) |
| ***C07D 403/10*** | (2006.01) |

(52) U.S. Cl.
CPC ............ *C07D 403/06* (2013.01); *C07D 403/10* (2013.01)

(58) Field of Classification Search
CPC ..................................................... C07D 233/02
USPC ...................................................... 548/314.7
See application file for complete search history.

(56) References Cited

U.S. PATENT DOCUMENTS

| | | | | |
|---|---|---|---|---|
| 5,411,981 | A | 5/1995 | Gaillard-Kelly et al. | |
| 2006/0287327 | A1 | 12/2006 | Labrie et al. | |
| 2007/0004753 | A1 | 1/2007 | Sawyers et al. | |
| 2009/0291965 | A1 | 11/2009 | Close et al. | |
| 2011/0077581 | A1* | 3/2011 | Oyelere et al. | 604/20 |

OTHER PUBLICATIONS

International Search Report and Written Opinion, PCT/US2011/053623, mailed Feb. 15, 2012.

* cited by examiner

*Primary Examiner* — Rebecca Anderson
*Assistant Examiner* — Karen Cheng
(74) *Attorney, Agent, or Firm* — Myers Bigel Sibley & Sajovec, PA

(57) ABSTRACT

Compounds of Formula (I), and methods of making and using thereof, are described herein; wherein AR is an aryl group, ZBG is a Zinc Binding Group, and other substituents are as defined herein. The compounds can be administered as a pharmaceutically acceptable salt, prodrug, or solvate. The compounds may be useful to treat and/or prevent hyperproliferative disorders which may include hormone sensitive and hormone refractory prostate cancers. The compounds can be formulated with a pharmaceutically acceptable carrier and, optionally one or more pharmaceutically acceptable excipients, for enteral or parenteral administration.

(I)

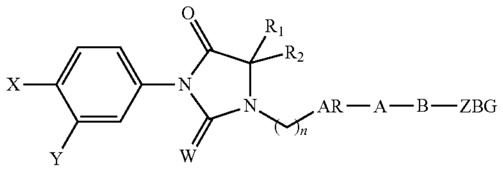

17 Claims, 4 Drawing Sheets

HISTONE DEACETYLASE (HDAC) INHIBITORS TARGETING PROSTATE TUMORS AND METHODS OF MAKING AND USING THEREOF

RELATED APPLICATIONS

This application is a 35 U.S.C. §371 national phase entry of PCT Application PCT/US2011/053623, filed Sep. 28, 2011, and published in English on Apr. 19, 2012, as International Publication No. WO 2012/050868, and which claims the benefit of U.S. Provisional Patent Application Ser. No. 61/387,183, filed Sep. 28, 2010, the disclosure of each of which is incorporated by reference herein in its entirety.

STATEMENT OF GOVERNMENT SUPPORT

This invention was made with Government support under Grant No. 1RO1CA131217-01A2. The US Government has certain rights to this invention.

FIELD OF THE INVENTION

The present invention generally relates to histone deacetylase (HDAC) inhibitors that target prostate tumor. More particularly, the invention describes a series of arylhydantoin derived HDAC inhibitors that target androgen positive prostate tumors through their interaction with androgen receptor to facilitate selective uptake into and/or retention in the tumor cell. The invention describes the methods for making and using thereof.

BACKGROUND OF THE INVENTION

Prostate cancer remains the most common form of cancer among all males in the US, with black men at highest risk (Jemal, A.; Siegel, R.; Ward, E.; Hao, Y.; Xu, J.; Thun, M. J., Cancer Statistics, 2009. *CA Cancer J Clin* 2009, caac.20006). It is also the second leading cause of cancer related deaths in the US among men, largely due to the progressively treatment resistant nature of the disease. Treatment options for early stage prostate cancer commonly involve various combinations of watchful waiting, radical prostatectomy, radiation therapy, and very importantly, androgen-deprivation therapy (ADT) (Georgi, P.; Ronald, L. H.; Joel, B. N., The Treatment of Prostate Cancer. . *Cancer Practice* 2001, 9 (6), 295-306). Prostate cancer is dependent upon androgen hormone steroids such as dihydrotestosterone (DHT) for sustaining and promoting growth. They do this by binding to the Androgen Receptor (AR) and localizing to the nucleus where it forms a complex that up regulates the transcription of critical genes. ADT is accomplished by either (i) administering antagonist to the AR that blocks androgen ligands (such as DHT), or by (ii) castration, in order to reduce the amount of testosterone available. Often both methods of ADT are used. However, the disease frequently advances to the much more lethal castration-resistant prostate cancer (CRPC), becoming resistant to these therapies by overexpressing ARs (Chen, C. D.; Welsbie, D. S.; Tran, C.; Baek, S. H.; Chen, R.; Vessella, R.; Rosenfeld, M. G.; Sawyers, C. L., Molecular determinants of resistance to antiandrogen therapy. *Nature Medicine* 2004, 10 (1), 33-39; Papatsoris, A. G.; Karamouzis, M. V.; Papavassiliou, A. G., Novel biological agents for the treatment of hormone-refractory prostate cancer (HRPC). *Current Medicinal Chemistry* 2005, 12 (3), 277-296). The expression levels of AR is about six-fold higher in castration resistant as compared to hormone-sensitive prostate cancer (inj a, M. J.; Savinainen, K. J.; Saramaki, O. R.; Tammela, T. L. J.; Vessella, R. L.; Visakorpi, T., Amplification and overexpression of androgen receptor gene in hormone-refractory prostate cancer. *Cancer Res.* 2001, 61 (9), 3550-3555). The effective treatment options for patients at this point have been exhausted. Options currently available for CRPC are supportive care, salvage endocrine manipulations, radiotherapy, radioactive isotopes, bisphosphonates and chemotherapy (Lara, P. N.; Meyers, F. J., Treatment options in androgen-independent prostate cancer. *Cancer Investigation* 1999, 17 (2), 137-144). These options are not curative.

The understanding that AR overexpression is one of the major causes of hormone refractory prostate cancer, and the dependency of the growth of the hormone refractory prostate on the binding of AR ligands, suggest that AR is a viable target for this form of malignancy. The preference of anti-androgen as agents for prostate cancer therapy is predicated on the selectivity and fewer side effects of these agents. The discovery and the use thereof of these anti-androgens have been well documented in several patents such as U.S. Pat. No. 7,709,517, U.S. Pat. No. 4,097,578, U.S. Pat. No. 5,411,981, U.S. Pat. No. 5,705,654, PCT International Applications WO 97/00071 and WO 00/17163, U.S. Published Patent Application No. 2004/0009969, U.S. Published Patent Application No. 2007/0004753, U.S. Published Patent Application No. 2008/0139634 and U.S. Published Patent Application No. 2010/0172975. However, the anti-androgens in common clinical use, such as bicalutamide (brand name: Casodex), have curative effects only on hormone sensitive prostate cancer and not on hormone refractory prostate cancer. The lack of the activity of most anti-androgens against refractory prostate cancer is partly due to their weak antagonist activities and strong agonist activities when AR is overexpressed as in refractory prostate cancer. The availability of AR inhibitors with more potent antagonistic activities and minimal agonistic activities has been described a viable approach to delay the progression and/or treat hormone refractory prostate cancer (U.S. Pat. No. 7,709,517, U.S. Published Patent Application No. 2007/0004753, U.S. Published Patent Application No. 2008/0139634 and U. S. Published Patent Application No. 2010/0172975). Alternatively, the current anti-androgens, including but not limiting to the more potent diarylhydantions described in U.S. Pat. No. 7,709,517, U.S. Published Patent Application No. 2007/0004753, U.S. Published Patent Application No. 2008/0139634 and U.S. Published Patent Application No. 2010/0172975, could be designed to incorporate a new cancer inhibiting moiety. Our molecular docking analysis revealed that prototypical simple HDAC inhibiting pharmacophores could ideally function as the new cancer inhibiting moiety (unpublished results).

The histone protein complex associates with DNA to form the higher order structure called chromatin. The histones are bound either loosely to form "beads on a string" that are accessible to transcriptional activity, or a tighter chromatin complex that reduces access to the genetic information. The genomic flux is regulated by the tightness of binding through modifications such as methylation, acetylation, or phosphorylation of the histones (Minucci, S.; Pelicci, P. G., Histone deacetylase inhibitors and the promise of epigenetic (and more) treatments for cancer. *Nat. Rev. Cancer* 2006, 6 (1), 38-51). Two families of proteins that are involved in controlling the extent of acetylation are histone acetyl transferases (HATs), which place an acetyl group onto the lysine of a histone protein, and histone deacetylases (HDACs), which remove it. There are 11 known isoforms of HDAC enzymes in Class I and II, which employ catalytic $Zn2+$ embedded in the active site. In many cancers, including prostate cancer, it has been observed that there is aberrant transcriptional silencing that is the result of HDAC enzymes being in unusually high abundance. The up regulation of HDAC activity has been connected with the down regulation of key onco-suppressor proteins (Martinez-Iglesias, O.; Ruiz-Llorente, L.; Sanchez-Martinez, R.; Garcia, L.; Zambrano, A.; Aranda, A., Histone deacetylase inhibitors: mechanism of action and therapeutic use in cancer. *Clin. Transl. Oncol.* 2008, 10 (7), 395-398).

HDAC inhibition has been validated as a clinically viable cancer therapy in recent years. Suberoylanilide hydroxamic acid (SAHA,) received FDA approval for treatment of cutaneous T-cell lymphoma in 2006, along with FK228 which gained approval in 2009. Many other HDACi are being enthusiastically investigated, with several clinical trials running currently (Richon, V. M.; Emiliani, S.; Verdin, E.; Webb, Y.; Breslow, R.; Rifkind, R. A.; Marks, P. A., A class of hybrid polar inducers of transformed cell differentiation inhibits histone deacetylases. *Proc. Natl. Acad. Sci. U.S.A.* 1998, 95 (6), 3003-3007; Tan, J. H.; Cang, S. D.; Ma, Y. H.; Petrillo, R. L.; Liu, D. L., Novel histone deacetylase inhibitors in clinical trials as anti-cancer agents. *J. Hematol. Oncol.* 2010, 3). One of the major drawbacks of present HDAC inhibitors is their lack of isoform, tissue, and cell type selectivity, resulting in toxicity and low potency. An approach that selectively target HDAC inhibitors to the diseased cells could ameliorate many of these drawbacks.

All HDAC inhibitors so far reported fit a three-motif pharmacophoric model namely, a zinc-binding group (ZBG), a hydrophobic linker and a recognition cap-group (Miller, T. A.; Witter, D. J.; Belvedere, S., *J. Med. Chem.*, 46, 5097-5116 (2003)). We have observed a convergence of structure activity relationship (SAR) between the aryl recognition cap-group of HDAC inhibitors and diarylhydantoin anti-androgens that enabled the design of arylhydantoin derived HDAC inhibitors (unpublished results). These arylhydantoin derived HDAC inhibitors, through the interactions between AR and their anti-androgen moiety, are expected to target androgen positive prostate tumors and become selectively uptaken into and/or retained in the tumor cell. This approach should provide a highly desirable treatment options that become increasingly more selective and potent as the disease progresses from the hormone sensitive to the hormone refractory stage.

It is therefore an object of the invention to provide arylhydantoin derived HDAC inhibitors with improved selectivity for prostate malignacies and methods of making and using thereof.

SUMMARY OF THE INVENTION

Compounds of Formula I, and methods of making and using thereof, are described herein.

(I)

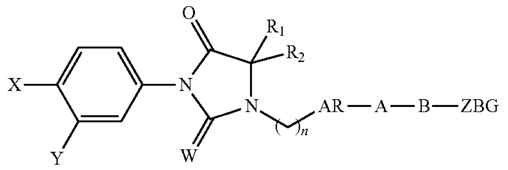

Wherein:

AR is an aryl group or a covalent bond;

n consists of $C_{0-6}$ group, optionally containing one or more heteroatoms, wherein the carbon atoms and/or heteroatoms are in a linear arrangement, A is a linking group connected to AR, B is an alkyl, alkylaryl or alkylheteroaryl spacer group, ZBG is a Zinc Binding Group, $R_1$ and $R_2$ are independently selected from groups consisting of hydrogen, and/or together from groups comprising 1-8 carbon atoms, selected from wherein these groups comprising 1-8 carbon atoms are selected from groups consisting of alkyl, substituted alkyl including haloalkyl, and, together with the carbon to which they are linked, a cycloalkyl or substituted cycloalkyl group, W is selected from the group consisting of O and S, X is selected from the group consisting of cyano and nitro, Y is selected from the group consisting of trifluoromethyl and iodo.

The compounds can be administered as a pharmaceutically acceptable salt, prodrug, or solvate. The compounds may be useful to treat and/or prevent hyperproliferative disorders which may include hormone sensitive and hormone refractory prostate cancers. The compounds described herein can be formulated with a pharmaceutically acceptable carrier and, optionally one or more pharmaceutically acceptable excipients, for enteral or parenteral administration.

DETAILED DESCRIPTION OF THE INVENTION

I. Definitions

Figure 1:
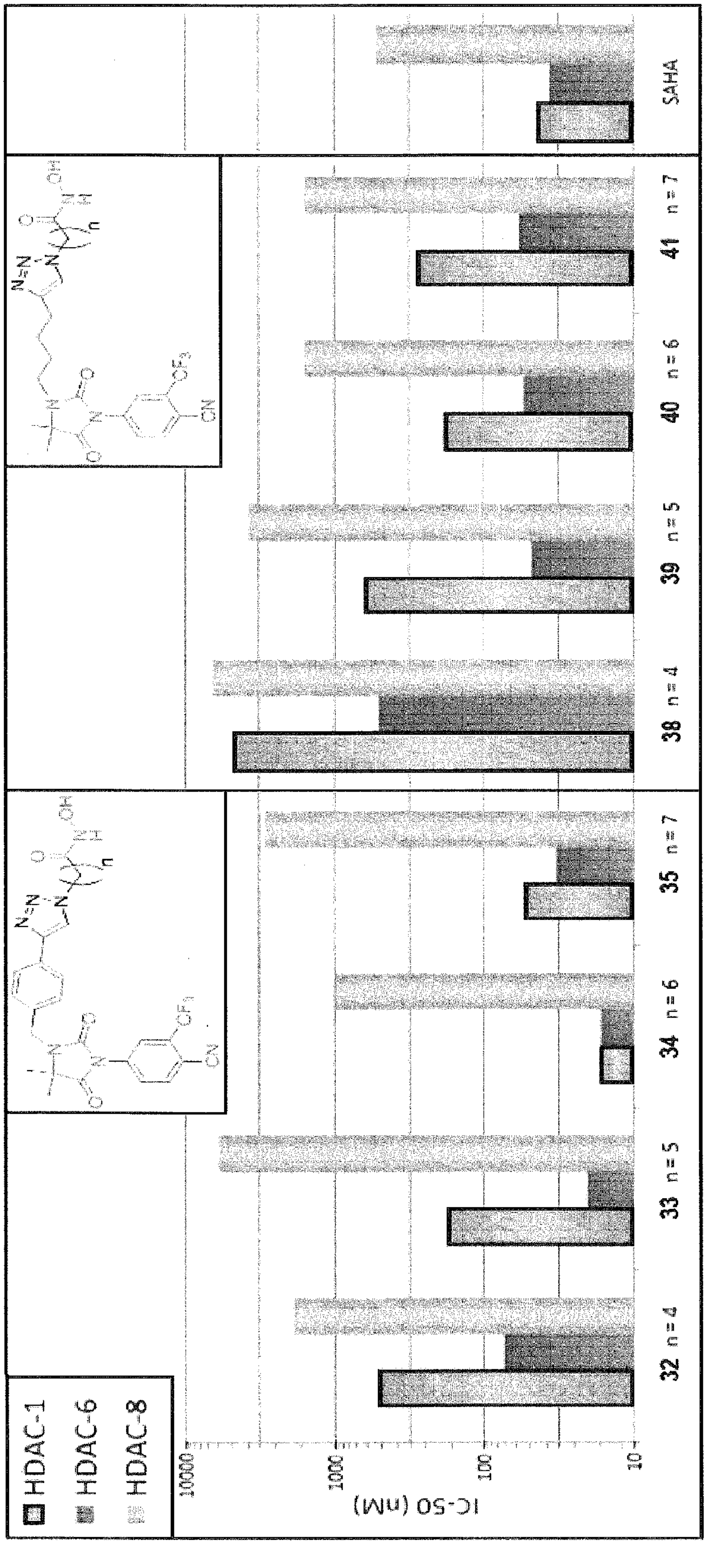
FIG. 1 shows the anti-HDAC activity of arylhydantoin derived HDAC inhibitors 32-35 and 38-41 against HDACs 1, 6 and 8 ($IC_{50}$ in nM).
Figure 2:
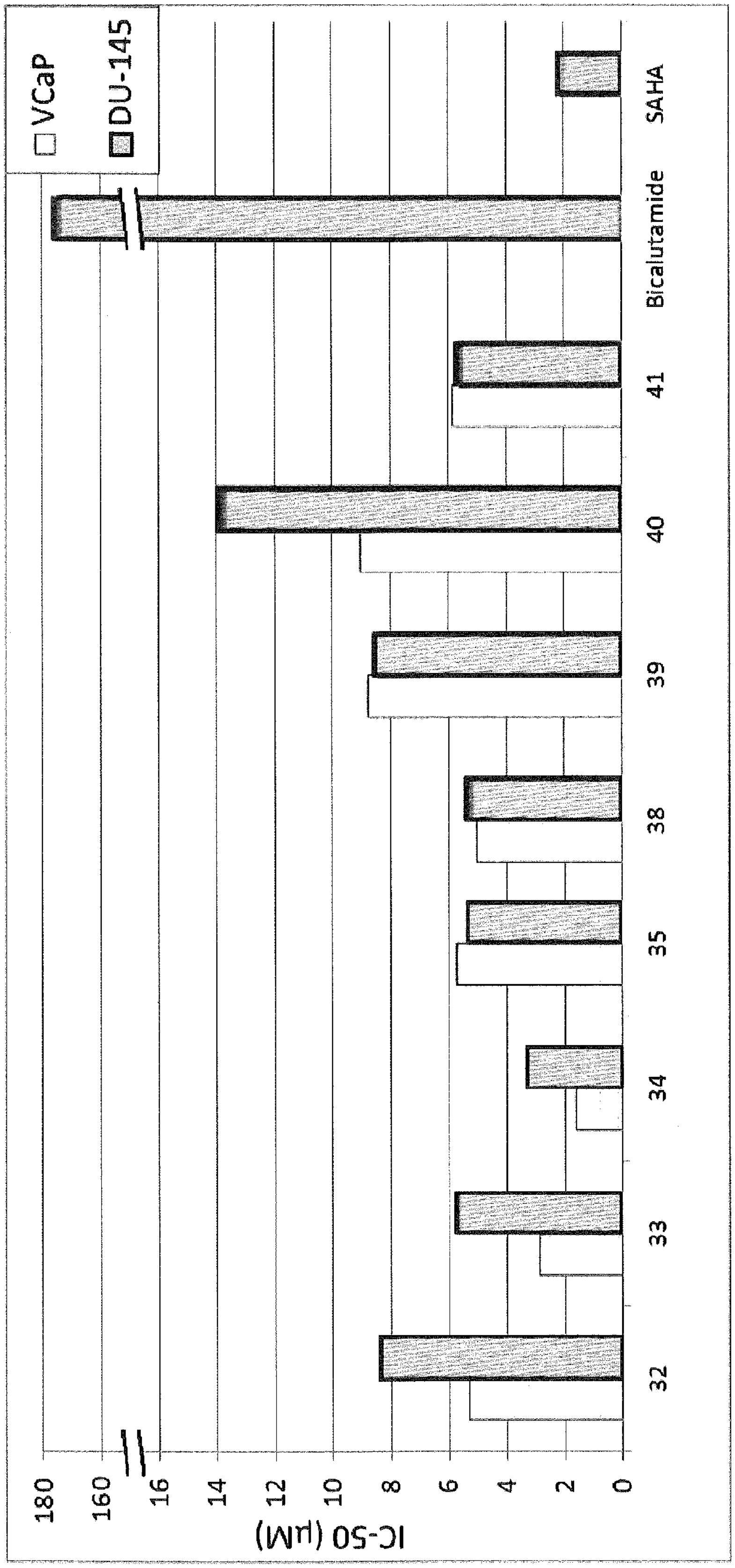
FIG. 2 shows the antiproliferative activity of arylhydantoin derived HDAC inhibitors 32-35 and 38-41 against VCaP and DU-145 prostate cancer cell lines ($IC_{50}$ in □M).

AR represents an aryl group. "Aryl", as used herein, refers to -, 6- and 7-membered aromatic, heterocyclic, fused aromatic, fused heterocyclic, biaromatic, or bihetereocyclic ring system, optionally substituted by halogens, alkyl-, alkenyl-, and alkynyl-groups. Broadly defined, "AR", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, alkyl, aralkyl, alkenyl, alkynyl, cycloalkyl, hydroxyl, alkoxyl, amino, nitro, sulfhydryl, imino, amido, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

The linking group A is chosen from amide, reverse amide, ester, reverse ester, alkoxyl, sulfanyl, sulfinyl, sulfonyl, sulfonamido, ketone, SP2 hybridized carbon, SP hybridized carbon, 5 or 6 membered heterocyclic rings including but not limiting to 1,2,3-triazolyl, 1,2,4-triazolyl, 1-tetrazolyl, 1-indolyl, 1-indazolyl, 2-isoindolyl, 7-oxo-2-isoimdolyl, 1-pirinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazolyl, 2-quinolyl. 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole. benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl. Each of these moieties may be substituted as appropriate.

B is an alkyl, alkylaryl or alkylheteroaryl spacer group. The alkyl spacer group chain length ranges from about $C_1$ to about $C_{11}$, optionally substituted by one or more double and/or triple bonds.

"Zinc binding group" or "ZBG", as used herein, refers to moieties capable of inhibiting zinc metalloenzymes activity including HDAC and matrix metalloproteinase (MMP) activity. Suitable examples include, but are not limited to, hydroxamates, N-formyl hydroxylamine (or retro-hydroxamate), carboxylates, thiols, dithiols, trithiocarbonates, thioesters, benzamide, keto, mercaptoacetamides, 2-ketoamides, epoxides, epoxyketones, trifluoromethyl ketones, hydroxypyridinones, pyrones, hydroxylpyridinethiones, and thiopyrones.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone. For example, C1 to C4 or C6 linear alkyl. Likewise, preferred cycloalkyls have from 3-10 carbon atoms in their ring structure, and more preferably have 5, 6 or 7 carbons in the ring structure, and optionally contain or are substituted with heteroatoms, such as with 1, 2, 3 or more independently selected oxygen, nitrogen, or sulfur atoms.

"Alkylaryl", as used herein, refers to an alkyl group substituted with an aryl group (e.g., an aromatic or hetero aromatic group).

"Acyl" or "acyl group" as used herein is intended to mean a —C(O)—R radical, where R is a suitable substituent (for example, an acetyl group, a propionyl group, a butyroyl group, a benzoyl group, or an alkylbenzoyl group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $(C_{1-4})$alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The terms "alkenyl" and "alkynyl" refer to unsaturated aliphatic groups analogous in length and possible substitution to the alkyls described above, but that contain at least one double or triple bond respectively.

The terms ortho, meta and para apply to 1,2-, 1,3- and 1,4-disubstituted benzenes, respectively. For example, the names 1,2-dimethylbenzene and ortho-dimethylbenzene are synonymous.

"Pharmaceutically acceptable salt", as used herein, refer to derivatives of the compounds defined by Formula I wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) which is administered in an inactive (or significantly less active) form. Once administered, the prodrug is metabolized in the body (in vivo) into the active compound.

"Solvate", as used herein, refers to a compound which is formed by the interaction of molecules of a solute with molecules of a solvent.

"Reverse ester", as used herein, refers to interchange in the positions of the oxygen and carbon groups in a series of structurally related compounds.

"Reverse amide", as used herein, refers to interchange in the positions of the nitrogen and carbon groups in a series of structurally related compounds.

II. Compounds

Compounds of Formula I, and methods of making and using thereof, are described herein.

(I)

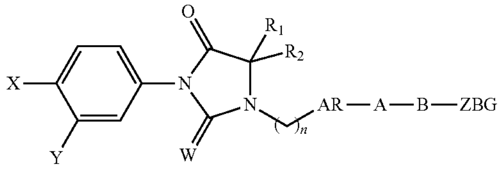

wherein:

AR is an aryl group or is absent (i.e., represents a covalent bond);

n consists of (or represents in conjunction with the structure shown in the associated parentheses, all of which can be replaced by a symbol or character such as B' as used below) a $C_{0-6}$ group, optionally containing one or more heteroatoms, wherein the carbon atoms and/or heteroatoms are in a linear arrangement (thus n can represent a covalent bond when C is O), A is a linking group connected to AR;

B is an alkyl, alkylaryl or alkylheteroaryl spacer group,

ZBG is a Zinc Binding Group, $R_1$ and $R_2$ are independently selected from groups consisting of hydrogen, and/or together from groups comprising 1-8 carbon atoms, selected from wherein these groups comprising 1-8 carbon atoms are selected from groups consisting of alkyl, substituted alkyl including haloalkyl, and, together with the carbon to which they are linked, a cycloalkyl or substituted cycloalkyl group, W is selected from the group consisting of O and S, X is selected from the group consisting of cyano and nitro, Y is selected from the group consisting of trifluoromethyl and iodo.

Thus particular examples of the foregoing include, but are not limited to, compounds of the Formulas Ia-Ik, as follows:

(Ia)
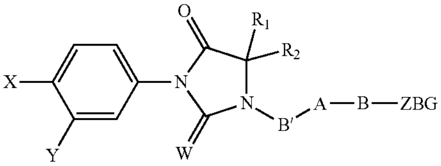
(Ib)
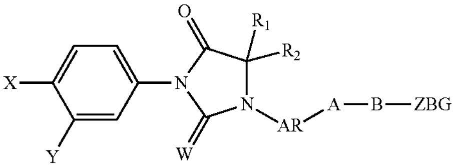
(Ic)
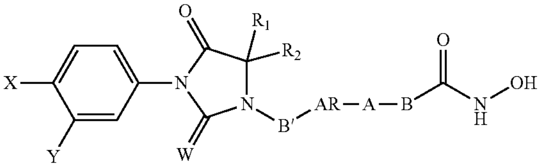
(Id)
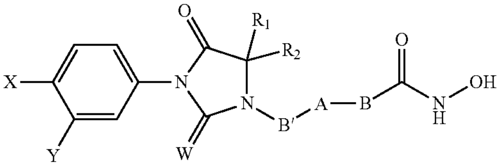
(Ie)
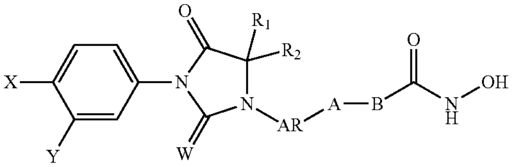
(If)
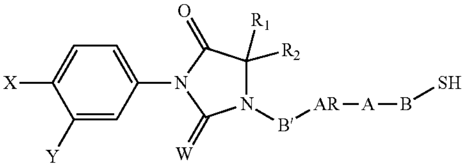
(Ig)
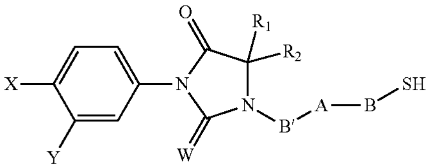
(Ih)
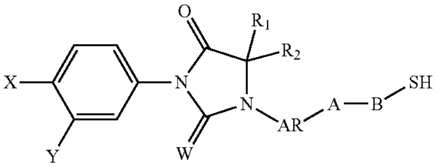
-continued
(Ii)
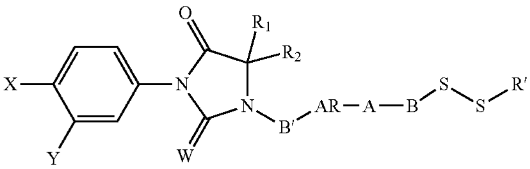
(Ij)
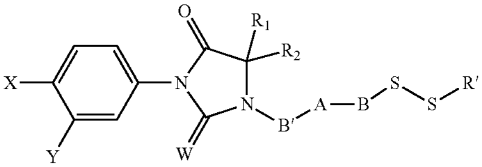
(Ik)
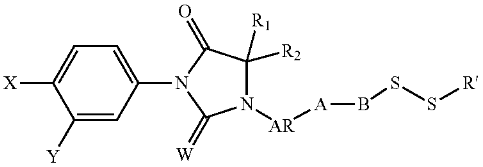
Where R' is acyl or alkyl; and where X, Y, W, $R_1$, $R_2$, B' (or n), AR, A, B, and ZBG are all as given above or as given below.
Examples of B', n, or the group represented by the structure:
,
include, but are not limited to, a covalent bond, C1 to C6 linear alkyl groups such as: $-CH_2-$, $-CH_2CH_2-$, $-CH_2CH_2CH_2-$, etc.
Examples of group AR include, but are not limited to:
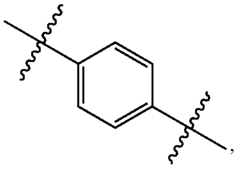, 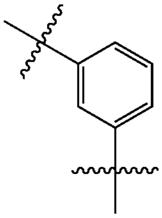,
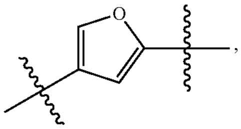, 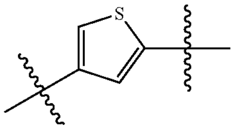,
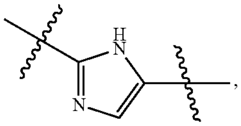, 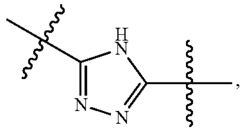,
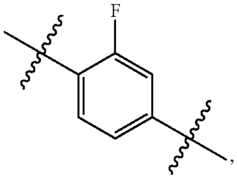, 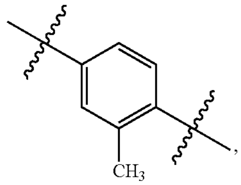, -continued

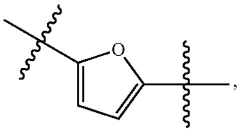, 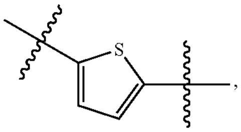,

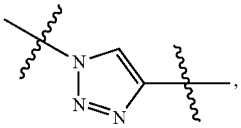, 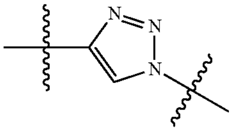,

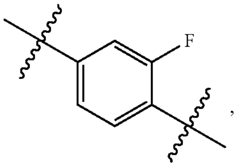, 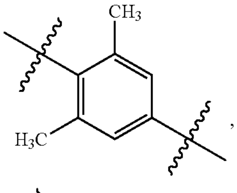,

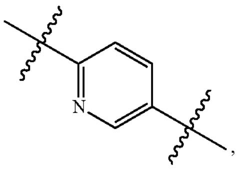, 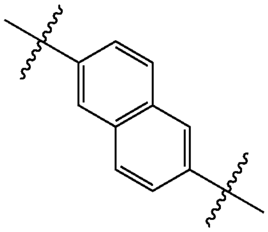,

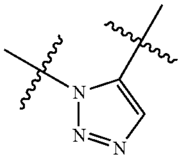, 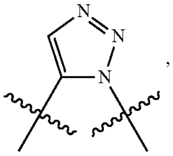,

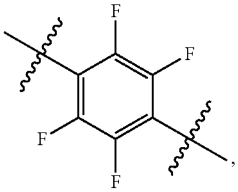, 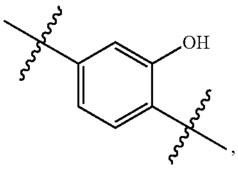,

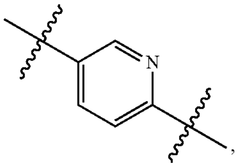, 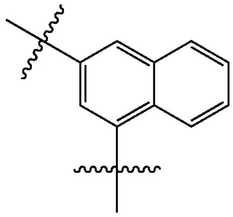,

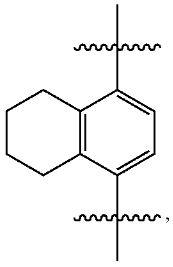, 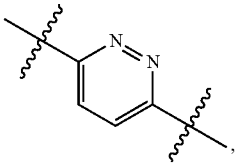,

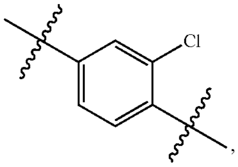, 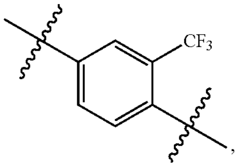,

-continued

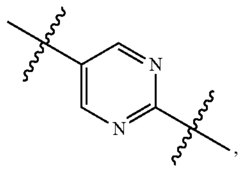, 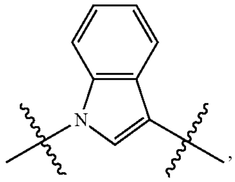,

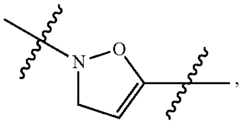, 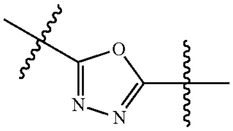,

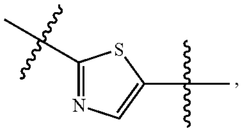, 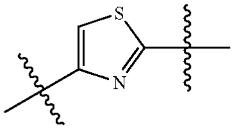.

The linking group A is chosen from amide, reverse amide, ester, reverse ester, alkoxyl, sulfanyl, sulfinyl, sulfonyl, sulfonamido, ketone, SP2 hybridized carbon, SP hybridized carbon, 5 or 6 membered heterocyclic rings including but not limiting to 1,2,3-triazolyl, 1,2,4-triazolyl, 1-tetrazolyl, 1-indolyl, 1-indazolyl, 2-isoindolyl, 7-oxo-2-isoimdolyl,1-pirinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazolyl, 2-quinolyl. 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole. benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-5-yl, 5-oxazolyl, 1-pyrrolyl, 1-pyrazolyl. Each of these moieties may be substituted as appropriate. Thus, examples of linking groups "A" include, but are not limited to:

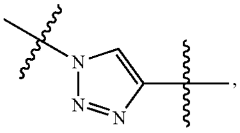, 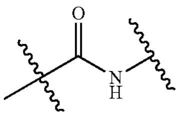,

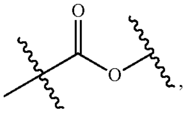, 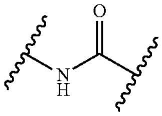, 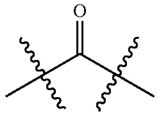,

-continued

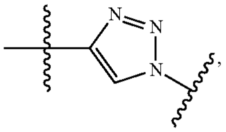,
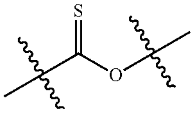,
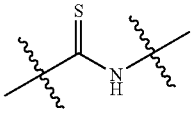,
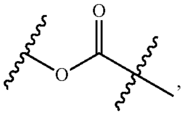,
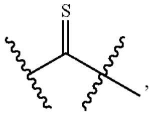,
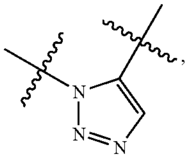,
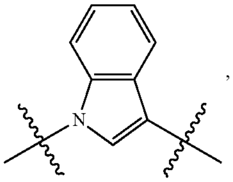,
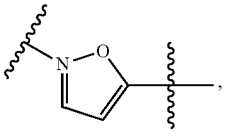,
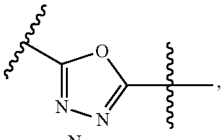,
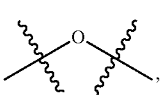,
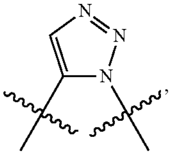,
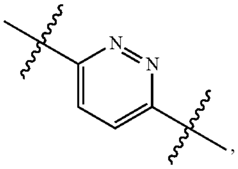,
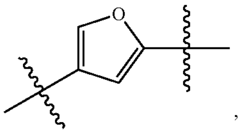,
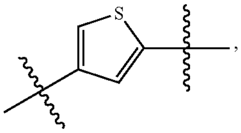,
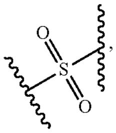,
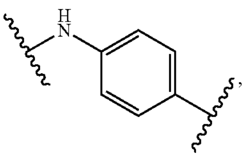,
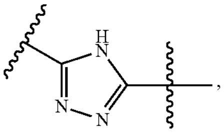,
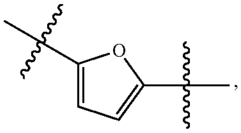,
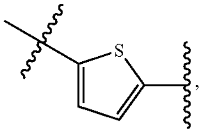, and
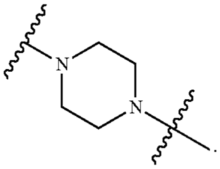.

where indicates optional connecting points to A and B', or to A and the nitrogen atom of the hydantoin group when B' is absent.

B is an alkyl, alkylaryl or alkylheteroaryl spacer group. The alkyl spacer group chain length ranges from about $C_1$ to about $C_{11}$, optionally substituted by one or more double and/or triple bonds. Thus, examples of spacer groups "B" include, but are not limited to, C1 or C2 to C6 or C8 linear alkyl, optionally containing one or more double or triple bonds and/or $—CH_3$, $—CH_2CH_3$ branchings.

"Zinc binding group" or "ZBG", as used herein, refers to moieties capable of inhibiting zinc metalloenzymes activity including HDAC and matrix metalloproteinase (MMP) activity. Suitable examples include, but are not limited to, hydroxamates, N-formyl hydroxylamine (or retro-hydroxamate), carboxylates, thiols, dithiols, trithiocarbonates, thioesters, benzamide, keto, mercaptoacetamides, 2-ketoamides, epoxides, epoxyketones, trifluoromethyl ketones, hydroxypyridinones, pyrones, hydroxylpyridinethiones, and thiopyrones. Thus examples of zinc binding groups include, but are not limited to, the following:

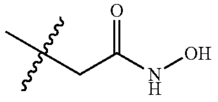
hydroxamic acids

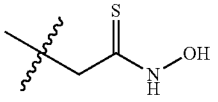
thiol-hydroxamic acids

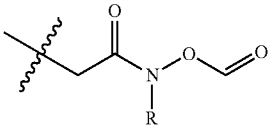
N-formyl hydroxylamines
where R is H, or alkyl such as methyl, ethyl, etc.

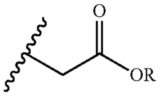
carboxylates
where R is H or a salt counter ion such as $Na^+$, etc

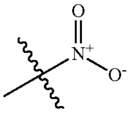
nitro

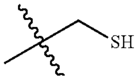
thiols

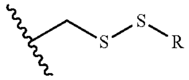
dithiols
R = Acyl such as ——$COCH_3$
or alkyl group such as methyl, ethyl, etc.

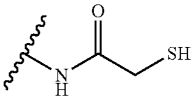
mercaptoacetamides

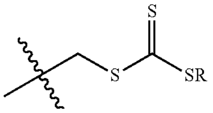
trithiocarbonates
where R is H or a salt counter ion such as $Na^+$, etc

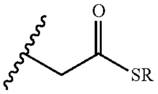
thioesters
R = Acyl such as ——$COCH_3$
or alkyl group such as methyl, ethyl, etc.

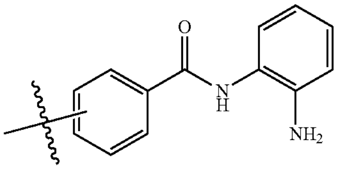
benzamides

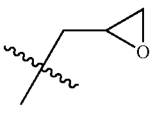
epoxides

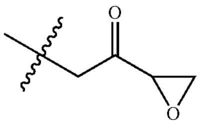
epoxyketones

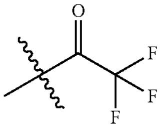
trifluoromethyl ketones

-continued

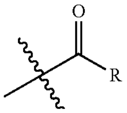

keto
where R is an alkyl group such as methyl, ethyl, etc.

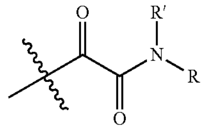

2-ketoamides
where R, R′ are independently H or alkyl such as methyl or ethyl

Particular examples of active compounds of the present invention are set forth in Table 1 below. Additional examples of active compounds of the present invention include, but are not limited to, the following:

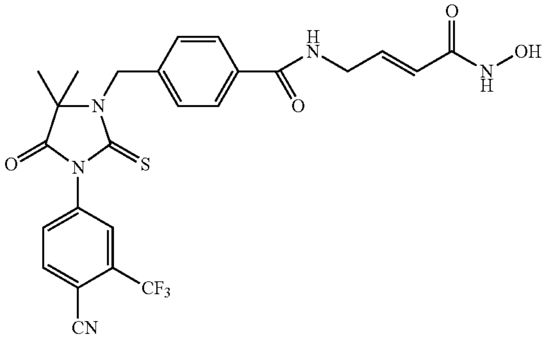

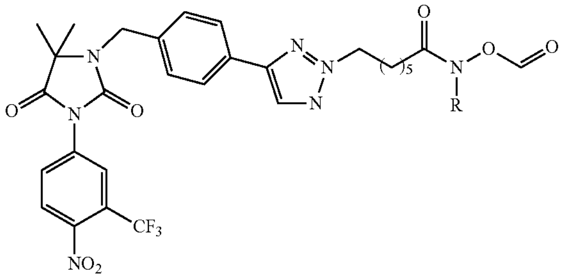

where R is H, methyl, or ethyl.

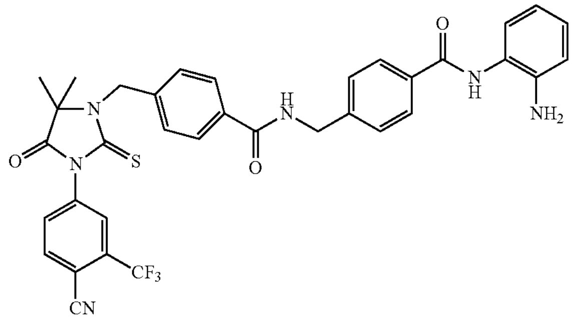

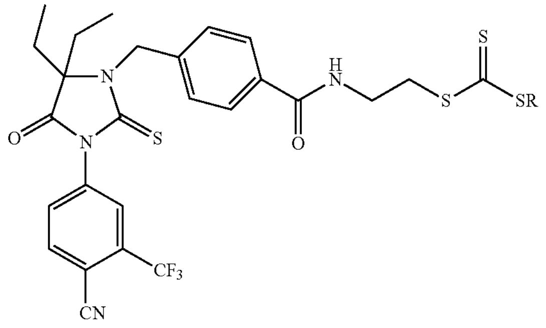

where R is H or a salt counter ion (ex $Na^+$, etc)

-continued

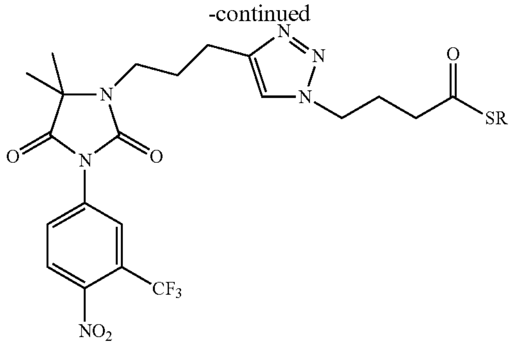

where R is acyl such as phenyl or alkyl such as methyl

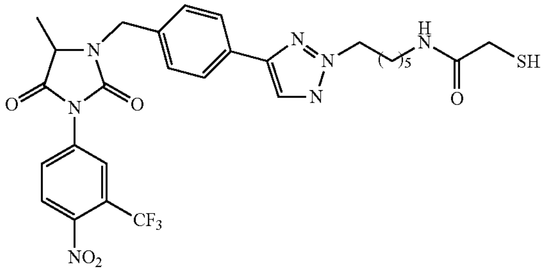

where R is H, methyl, or ethyl.

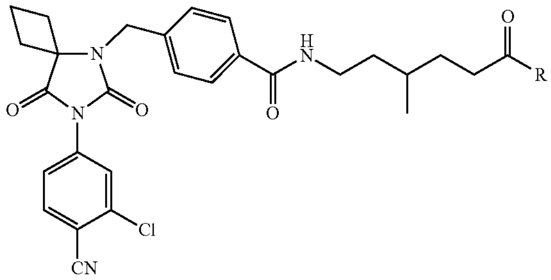

where R is alkyl such as methyl or phenyl

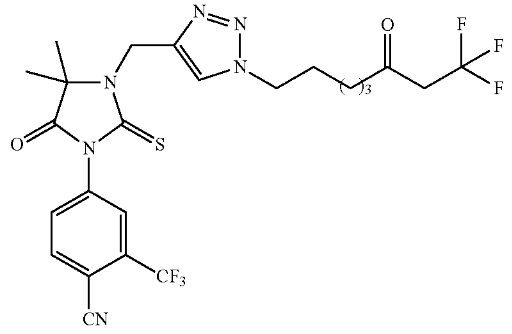

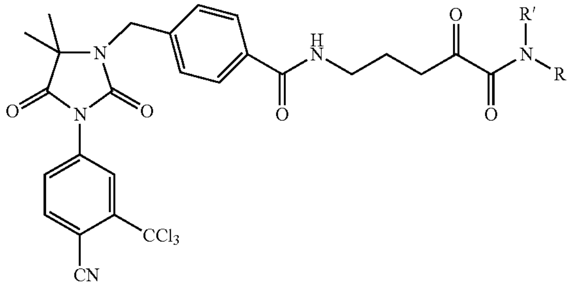

where R and R′ are independently H or alkyl such as methyl or ethyl

-continued

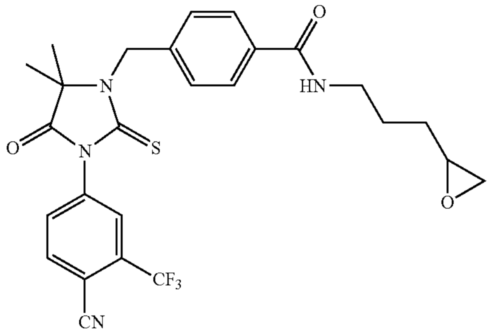

-continued

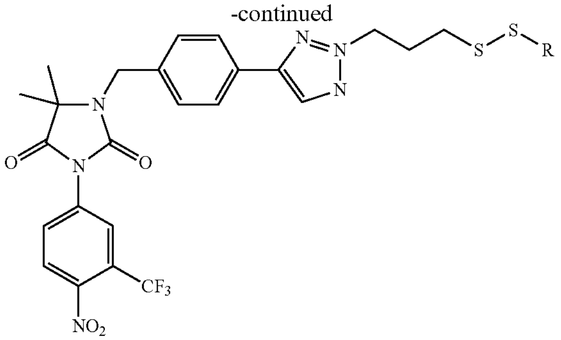

where R is acyl or alkyl such as methyl or phenyl

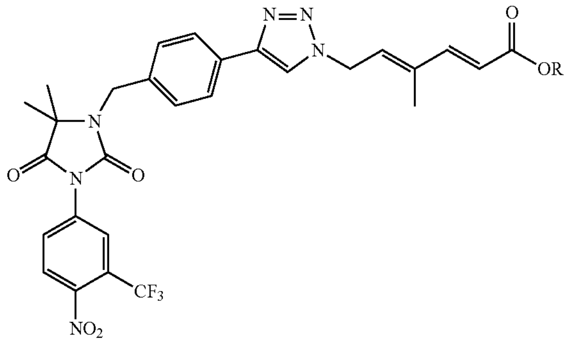

where R is H or a salt Counter ion (ex $Na^+$, etc)

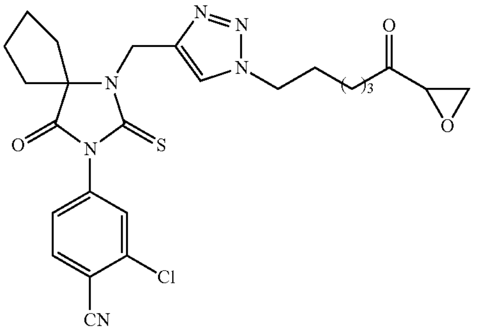

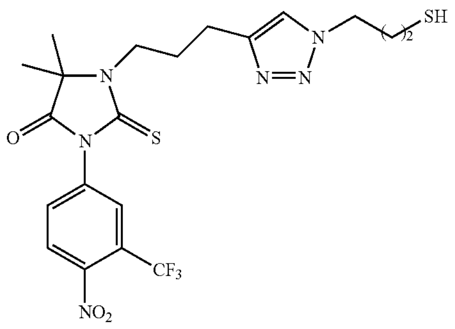

III. Formulations and Administration

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The present invention is primarily concerned with the treatment of human subjects, but the invention may also be carried out on animal subjects, particularly mammalian subjects such as dogs, cats, livestock and horses for veterinary purposes.

While subjects may be of any suitable age, the subjects are in some embodiments neonatal, infant, juvenile, adolescent, adult, or geriatric subjects.

These compounds may be used as anti-cancer treatment for carcinomas, especially those found to express or over-express the androgen receptor or the GCPR6A receptor, which includes, but is not limited to breast cancers, pancreatic cancers and prostate cancers. They may also find use in treatment of other androgen-related conditions including, but not limited to, baldness, muscular dystrophy/atrophy, mental cognition, acne, substance abuse/addiction and behavioral disorders.

The therapeutically effective dosage of any specific compound, will vary somewhat from compound to compound, and patient to patient, and will depend upon the condition of the patient and the route of delivery. As a general proposition, a dosage from about 0.1 to about 100 or 200 mg/kg may be used, with all weights being calculated based upon the weight of the active compound, including the cases where a salt is employed. Toxicity concerns at the higher level may restrict intravenous dosages to a lower level such as up to about 10 or 20 mg/kg, with all weights being calculated based upon the weight of the active base, including the cases where a salt is employed. In some embodiments, a dosage from about 5 or 10 mg/kg to about 50 or 100 mg/kg may be employed for oral administration.

Other Active Agents.

The arylhydantoin derived HDAC inhibitors described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the inhibitors can be administered in the same dosage form or in separate dosage forms with one or more other active agents.

Specific examples of compounds that can be adjunctively administered with the inhibitors include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextro amphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenyloin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

EXAMPLES

α-Bromoalkanoic acids and 7-bromoheptane nitrile were purchased from Sigma-Aldrich. Nuclear magnetic resonance (NMR) spectra were recorded on a Varian-Gemini 400 magnetic resonance spectrometer. $^1H$ NMR spectra were recorded in parts per million (ppm) relative to the peak of $CDCl_3$, (7.24 ppm), $CD_3OD$ (3.31 ppm), or DMSO-$d_6$ (2.49 ppm). $^{13}C$ spectra were recorded relative to the central peak of the $CDCl_3$ triplet (77.0 ppm), $CD_3OD$ (49.0 ppm), Acetone-$d_6$ septet (29.84 ppm) or the DMSO-$d_6$ septet (39.7 ppm), and were recorded with complete hetero-decoupling. Multiplicities are described using the abbreviation s, singlet; d, doublet, t, triplet; q, quartet; m, multiplet; and app, apparent. High-resolution mass spectra were recorded at the Georgia Institute of Technology mass spectrometry facility in Atlanta. Common reaction solvents were either high performance liquid chromatography (HPLC) grade or American Chemical Society (ACS) grade, and used without further purification. "Preparative TLC" or "prep TLC" refers to preparative thin layer chromatography and was performed on Analtech preparative TLC plates (UV 254, 2000 μm), unless otherwise stated. "Column chromatography" or "flash column chromatography" was performed with 200-400 Mesh silica gel, unless otherwise noted. UV light was used to examine the spots. Silica gel (200-400 Mesh) was used in column chromatography.

Compound numberings, e.g., 1, 2, 3, etc. as used in this example and method of preparation sections of the present application and entitled "Examples" and "IV. Methods of Preparation", are for reference within these sections only do not describe and are not to be confused with any similar numberings in other section of the present application.

Compounds synthesized in accordance with the current invention are listed in Table 1.

TABLE 1

| Compound | Structure |
|---|---|
| 31 | 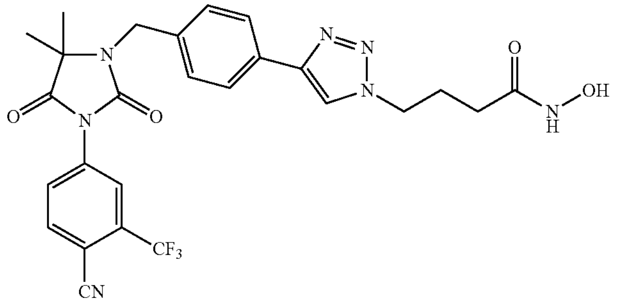 [SMILES: CC1(C)C(=O)N(c2ccc(C#N)c(C(F)(F)F)c2)C(=O)N1Cc1ccc(-c2cn(CCCC(=O)NO)nn2)cc1] |
| 32 | 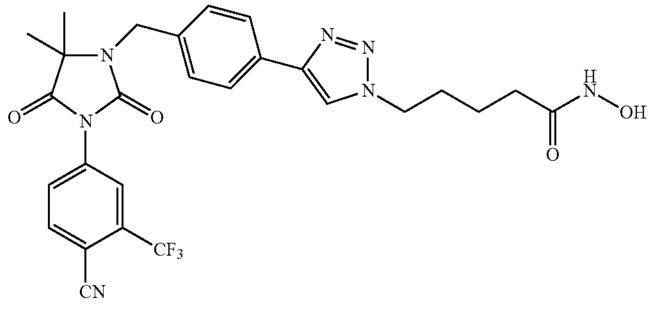 [SMILES: CC1(C)C(=O)N(c2ccc(C#N)c(C(F)(F)F)c2)C(=O)N1Cc1ccc(-c2cn(CCCCC(=O)NO)nn2)cc1] |

TABLE 1-continued
| Compound | Structure |
| --- | --- |
| 33 | 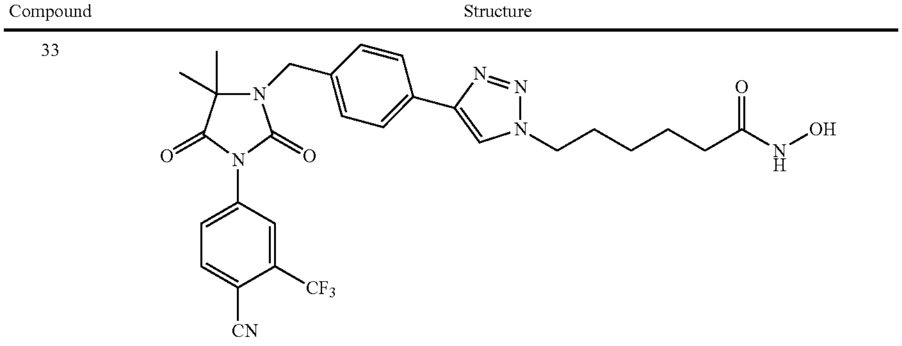 |
| 34 | 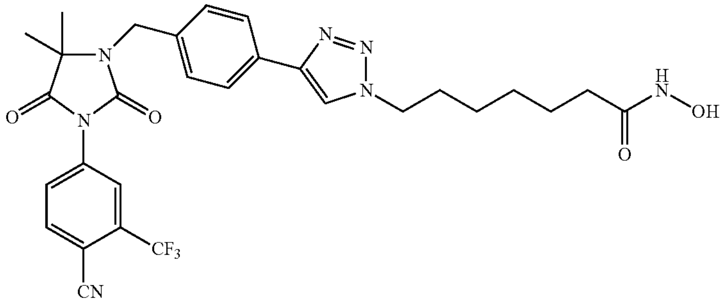 [SMILES: CC1(C)C(=O)N(c2ccc(C#N)c(C(F)(F)F)c2)C(=O)N1Cc1ccc(-c2cn(CCCCCCC(=O)NO)nn2)cc1] |
| 35 | 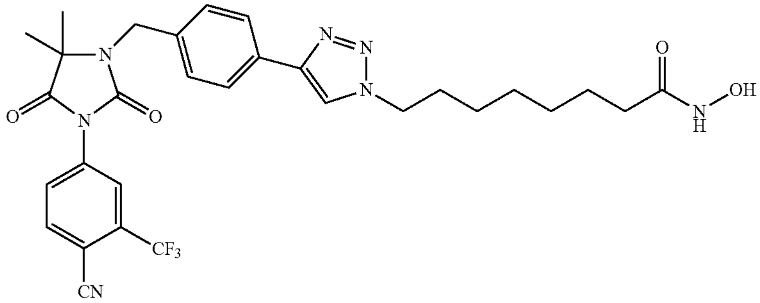 [SMILES: CC1(C)C(=O)N(c2ccc(C#N)c(C(F)(F)F)c2)C(=O)N1Cc1ccc(-c2cn(CCCCCCCC(=O)NO)nn2)cc1] |
| 36 | 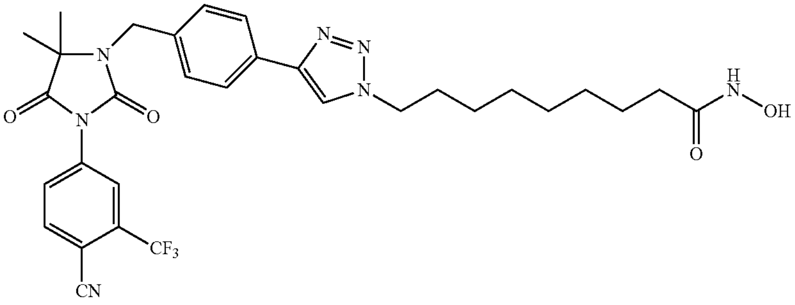 [SMILES: CC1(C)C(=O)N(c2ccc(C#N)c(C(F)(F)F)c2)C(=O)N1Cc1ccc(-c2cn(CCCCCCCCC(=O)NO)nn2)cc1] |

TABLE 1-continued
| Compound | Structure |
|---|---|
| 37 | 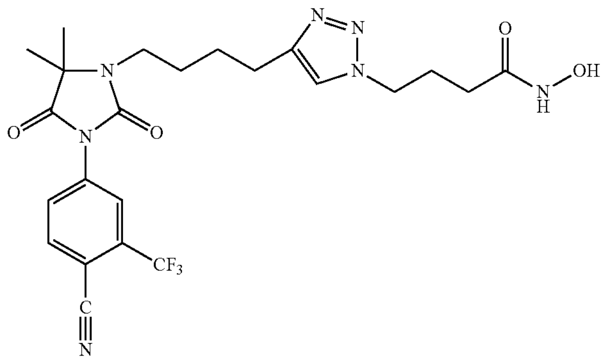 [SMILES: CC1(C)C(=O)N(c2ccc(C#N)c(C(F)(F)F)c2)C(=O)N1CCCCc1cn(CCCC(=O)NO)nn1] |
| 38 | 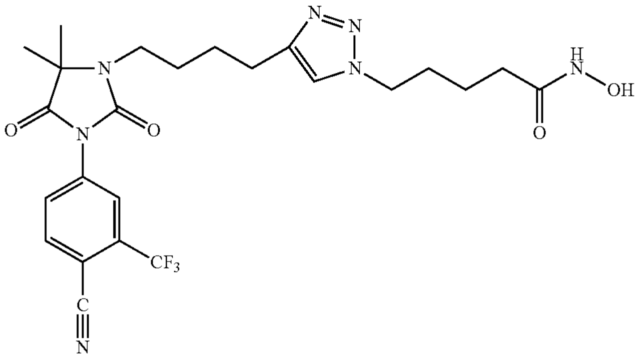 [SMILES: CC1(C)C(=O)N(c2ccc(C#N)c(C(F)(F)F)c2)C(=O)N1CCCCc1cn(CCCCC(=O)NO)nn1] |
| 39 | 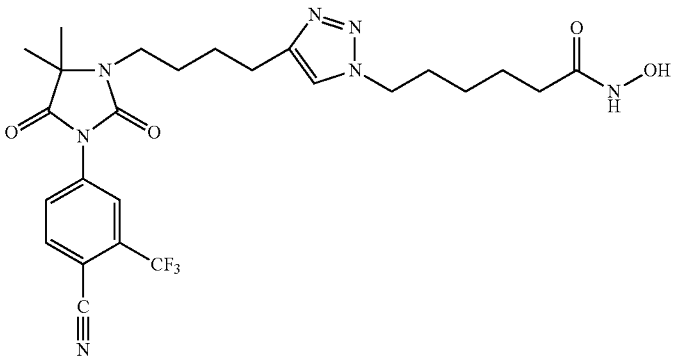 [SMILES: CC1(C)C(=O)N(c2ccc(C#N)c(C(F)(F)F)c2)C(=O)N1CCCCc1cn(CCCCCC(=O)NO)nn1] |
| 40 | 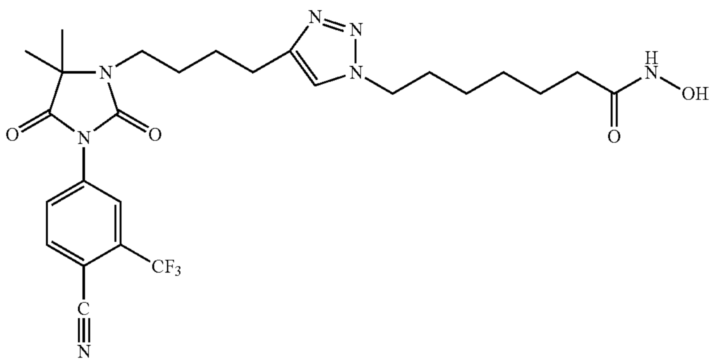 [SMILES: CC1(C)C(=O)N(c2ccc(C#N)c(C(F)(F)F)c2)C(=O)N1CCCCc1cn(CCCCCCC(=O)NO)nn1] |

TABLE 1-continued
| Compound | Structure |
|---|---|
| 41 | 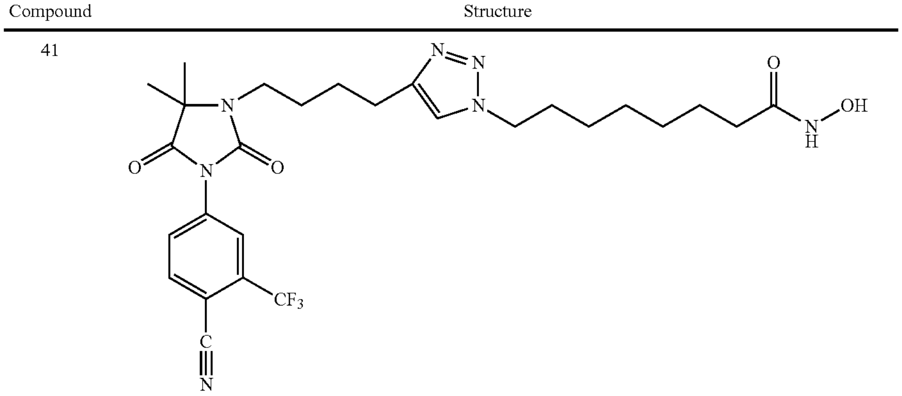 |
| 42 | 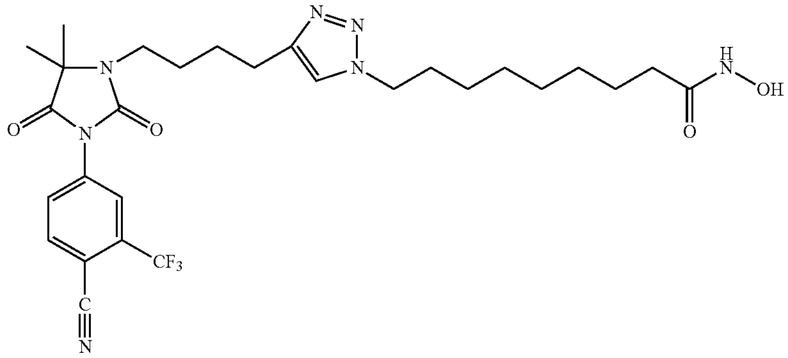 |
IV. Methods of Preparation
Example 1
Synthesis of Compounds 31-42
Scheme 1 below illustrates the synthesis of compounds 31-42.
SCHEME 1
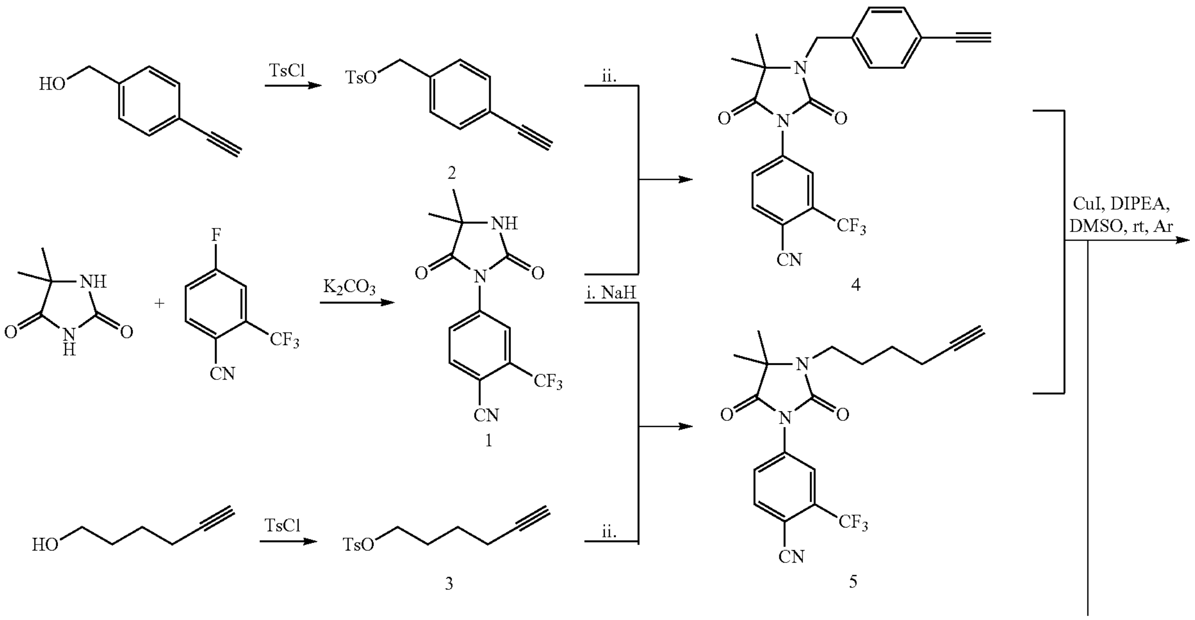

-continued
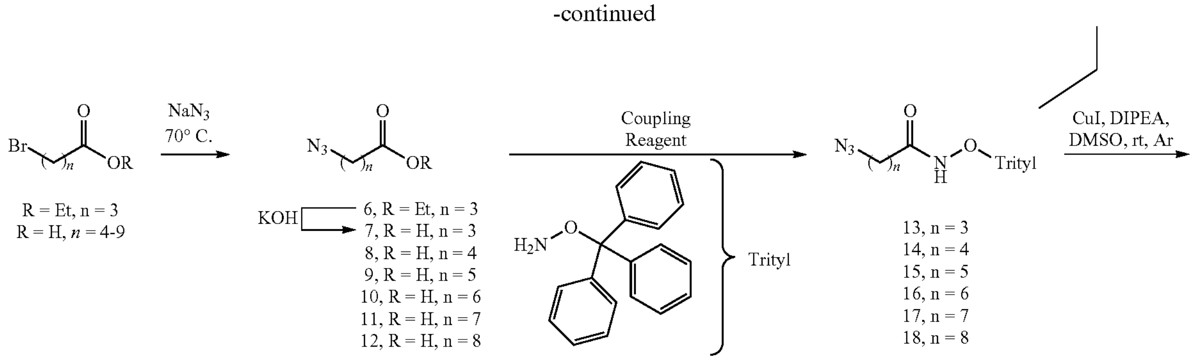
R = Et, n = 3
R = H, n = 4-9
6, R = Et, n = 3
7, R = H, n = 3
8, R = H, n = 4
9, R = H, n = 5
10, R = H, n = 6
11, R = H, n = 7
12, R = H, n = 8
13, n = 3
14, n = 4
15, n = 5
16, n = 6
17, n = 7
18, n = 8
PANEL 1 OF 2
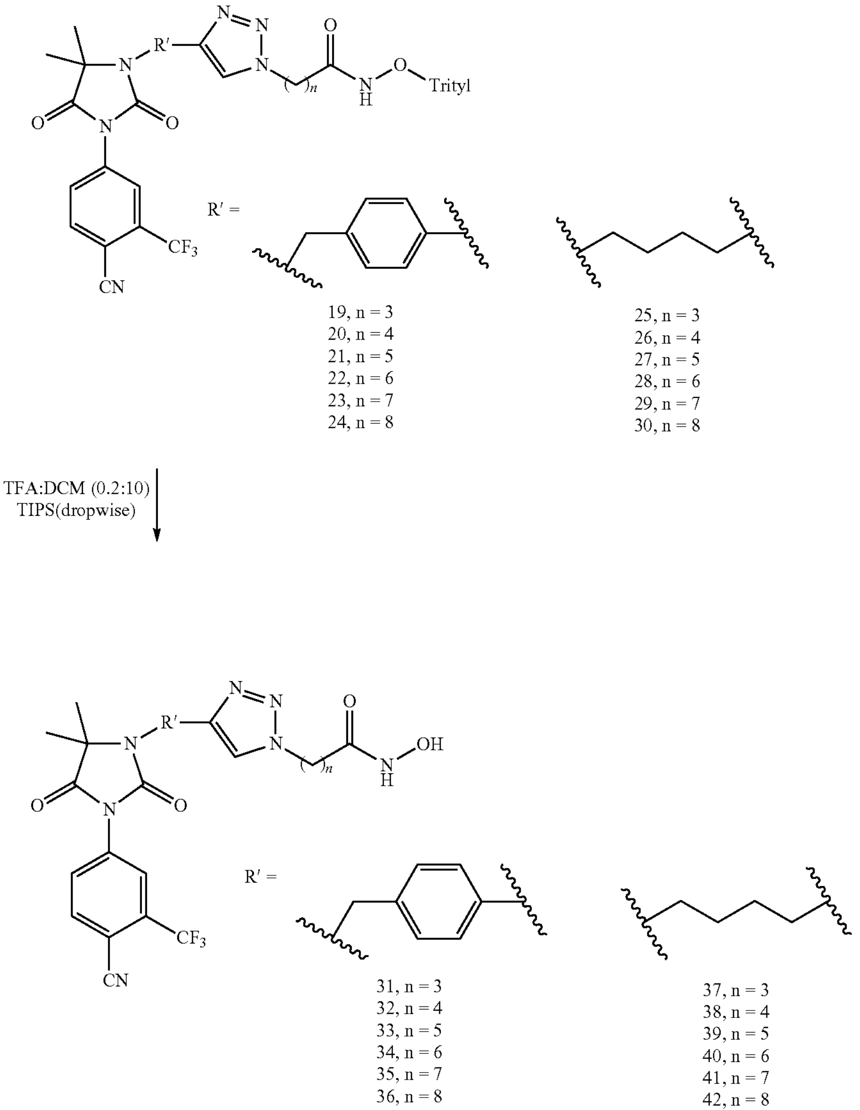
19, n = 3
20, n = 4
21, n = 5
22, n = 6
23, n = 7
24, n = 8
25, n = 3
26, n = 4
27, n = 5
28, n = 6
29, n = 7
30, n = 8
31, n = 3
32, n = 4
33, n = 5
34, n = 6
35, n = 7
36, n = 8
37, n = 3
38, n = 4
39, n = 5
40, n = 6
41, n = 7
42, n = 8
PANEL 2 OF 2

1

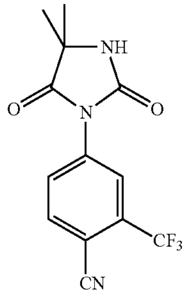

Procedure for synthesis of cyano-nilutamide (1)

(Cogan, P. S.; Koch, T. H. Rational Design and Synthesis of Androgen Receptor-Targeted Nonsteroidal Anti-Androgen Ligands for the Tumor-Specific Delivery of a Doxorubicin-Formaldehyde Conjugate. *J. Med. Chem.* 2003, 46, 5258-5270) 4-Fluoro-2-(trifluoromethyl)benzonitrile (4.02 g, 21.3 mmol) was added to Hydantoin (13.6 g, 106.3 mmol) and Potassium Carbonate (4.40 g, 31.9 mmol) in 60 mL DMF and stirred at 45° C. under argon for 48 hours. Reaction mixture was then diluted in ethyl acetate and washed three times with water. Organic layer was dried over sodium sulfate, filtered and concentrated in vacuo. Column chromatography (eluent 30:1 DCM/Methanol) gave 1 as a white solid (4.62 g, 74%). $^1$H NMR (400 MHz, $(CD_3)_2$—CO) δ 1.54 (6H, s), 7.80 (1H, s), 8.13 (1H, dd, J=1.8 Hz, J=8.4 Hz), 8.20 (1H, d, J=8.4 Hz), 8.26 (1H, d, J=1.8 Hz)

2

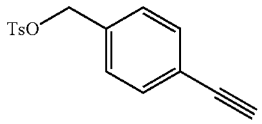

Procedure for Conversion of 4-Ethynylbenzyl Alcohol into 4-Ethynylbenzyl tosylate (2)

4-Ethynylbenzyl alcohol (2.59 g, 19.59 mmol) was dissolved in 200 mL THF. Potassium hydroxide (11.0 g, 195.9 mmol) and tosylchloride (11.2 g, 58.8 mmol) were added while stirring, and reacted for 12 hours at ambient temperature. Solids were then filtered off, and solution was concentrated in vacuo. Column chromatography (eluent 10:1 hexanes/EtOAc), followed by recrystallization in hexane/EtOAc gave 2 as an off white solid (2.74 g, 49%). $^1$H NMR ($CDCl_3$, 400 MHz) δ 2.37 (3H, s), 3.11 (1H, s), 5.00 (2H, s), 7.16 (2H, d, J=8.0), 7.28 (2H, d, J=8.0), 7.37 (2H, d, J=8.0), 7.74 (2H, d, J=8.0).

3

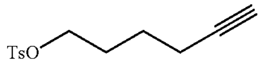

Procedure for Conversion of 5-Hexynyl alcohol into 5-Hexynyl tosylate (3)

5-Hexynyl alcohol (3.00 g, 30.6 mmol), triethylamine (4.64 g, 45.8 mmol) and tosylchloride (8.74 g, 45.8 mmol) were dissolved in 100 mL DCM, followed by addition of catalytic 4-dimethylaminopyridine. Reaction stirred for 48 hours at ambient temperature, then solution was washed with 200 mL $H_2O$, 150 mL saturated aqueous $NH_4Cl$, and lastly 150 mL brine. Organic layer was dried over sodium sulfate, filtered and concentrated in vacuo. Column chromatography (eluent 12:1 hexanes/EtOAc) gave 3 as a clear liquid (6.95 g, 90%). $^1$H NMR (400 MHz, $CDCl_3$) δ 1.37-1.60 (2H, m), 1.61-1.81 (2H, m), 1.89 (1H, s), 2.10 (2H, t, J=5.5 Hz), 2.39 (3H, s), 4.00 (2H, t, J=6.1 Hz), 7.30 (2H, d, J=7.8 Hz), 7.73 (2H, d, J=7.9 Hz) ppm.

4

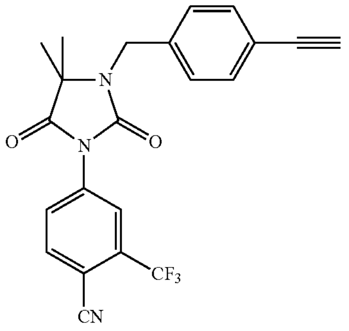

5

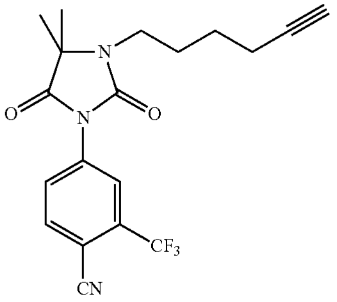

Representative Procedure for Synthesis of Cyano-Nilutamide-Alkynes. 4-[3-[(4-ethynylphenyl)methyl]-4,4-dimethyl-2,5-dioxo-1-imidazolidinyl]-2-(trifluoromethyl)-benzonitrile (4)

Compound 1 (565.2 mg, 1.90 mmol) was dissolved in 7 mL DMF under argon, followed by addition of NaH (60% in mineral oil, 129.3 mg, 3.23 mmol) and stirring for 2 hours at ambient temperature. Then 2 (1,089 mg, 3.80 mmol) was added and reaction was stirred for 11 hours at 53° C. Mixture was then dissolved in 100 mL 3:1 EtOAc/hexanes and washed 3 times with 150 mL brine. Organic layer was dried over sodium sulfate, filtered and concentrated in vacuo. Column chromatography (eluent 3:1 hexanes/EtOAc) gave 4 as a white solid (537.9 mg, 69%). $^1$H NMR (400 MHz, $CDCl_3$) δ 1.37 (6H, s), 3.09 (1H, s), 4.57 (2H, s), 7.30 (2H, d, J=8.4 Hz), 7.41 (2H, d, J=8.3 Hz), 7.86 (1H, d, J=8.4 Hz), 8.00 (1H, dd, J=1.9, 8.4 Hz), 8.14 (1H, d, J=7.3 Hz) ppm.

4-[3-(4-ethynylbutyl)-4,4-dimethyl-2,5-dioxo-1-imidazolidinyl]-2-(trifluoromethyl)benzonitrile (5)

Reaction of 1 (1.00 g, 3.364 mmol) with NaH and then 3 (1.697 g, 6.728 mmol) as described for the synthesis of 4, followed by column chromatography (eluent 3:1 hexanes/EtOAc) gave 4 as a white solid (1.154 g, 90%). $^1$H NMR (400

MHz, cdcl3) δ 1.50 (5H, s), 1.52-1.63 (2H, m), 1.67-1.85 (2H, m), 1.88-2.02 (1H, m), 2.05-2.33 (2H, m), 3.18-3.46 (2H, m), 7.87 (1H, d, J=8.4 Hz), 7.97 (1H, dd, J=1.8, 8.4 Hz), 8.11 (1H, d, J=1.5 Hz) ppm.

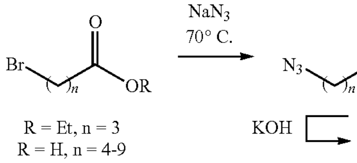

R = Et, n = 3
R = H, n = 4-9

6, R = Et, n = 3
7, R = H, n = 3
8, R = H, n = 4
9, R = H, n = 5
10, R = H, n = 6
11, R = H, n = 7
12, R = H, n = 8

Representative Procedure for Synthesis of ω-Azidoalkanoic Acids. 4-Azidobutanoic acid (7)

Ethyl 4-bromobutanoate (17.11 g, 87.7 mmol) and $NaN_3$ (28.50 g, 438.5 mmol) was dissolved in 70 mL DMF and reacted at 77° C. for 30 hours. 250 mL of 4:1 EtOAc/hexanes was added, and was washed twice with 250 mL saturated aqueous sodium bicarbonate, and once with 200 mL water. Organic layer was dried over sodium sulfate, filtered and concentrated in vacuo to give ethyl 4-azidobutanoate 6 (13.26 g, 96%). Ethyl 4-azidobutanoate 6 (6.18 g, 39.29 mmol) was then saponified using excess KOH in 12:10 methanol/water at 0° C. for 5 minutes and then ambient temperature for 11 hours, followed by acid workup to yield 4-Azidobutanoic acid 7 (4.69 g, 92%). $^1$H NMR (400 MHz, cdcl3) δ 1.71-1.98 (2H, m), 2.45 (2H, t, J=7.2 Hz), 3.35 (2H, t, J=6.7 Hz), 11.21 (1H, s) ppm.

5-Azidopentanoic acid (8)

Reaction of 5-bromopentanoic acid and $NaN_3$, as described for the synthesis of 6, gave 5-azidobutanoic acid 8. Saponification was not necessary. Used without further purification.

6-Azidohexanoic acid (9)

Reaction of 6-bromohexanoic acid and $NaN_3$, as described for the synthesis of 6, gave 6-Azidohexanoic acid 9. Saponification was not necessary. Used without further purification.

7-Azidoheptanoic acid (10)

Reaction of 7-bromoheptanoic acid and $NaN_3$, as described for the synthesis of 6, gave 5-azidoheptanoic acid 10. Saponification was not necessary. Used without further purification.

8-Azidooctanoic Acid (11)

Reaction of 8-bromooctanoic acid and $NaN_3$, as described for the synthesis of 6, gave 8-azidooctanoic acid 11. Saponification was not necessary. Used without further purification.

9-Azidononanoic Acid (12)

Reaction of 9-bromononanoic acid and $NaN_3$, as described for the synthesis of 6, gave 5-azidobutanoic acid 12. Saponification was not necessary. Used without further purification.

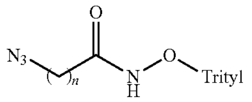

13, n = 3
14, n = 4
15, n = 5
16, n = 6
17, n = 7
18, n = 8

Procedure for Conversion of 4-Azidobutanoic Acid to 4-Azido-O-tritylbutylhydroxamate (13)

4-azidobutanoic acid 7 (1.01 g, 7.843 mmol), TBTU (4.197 g, 13.07 mmol) and diisopropylethylamine (1.689 g, 13.07 mmol) were added to 100 mL DCM at ambient temperature. O-tritylhydroxylamine (1.80 g, 6.536 mmol) was added last, and reaction stirred for 10 hours. Solvent was removed in vacuo, and column chromatography (eluent 4:1 hexanes/EtOAc) gave 13 as a clear semi-solid (2.53 g, 91.2%). $^1$H NMR (400 MHz, cdcl3) δ 1.42-1.61 (2H, m), 1.60-1.80 (2H, m), 2.86-3.18 (2H, m), 7.21-7.61 (15H, m), 7.78 (1H, s) ppm.

Representative procedure for conversion of ω-azidoalkanoic acids to O-trityl hydroxamates. 5-Azido-O-tritylpentahydroxamate (14)

5-azidopentanoic acid 1a (1.1 g, 7.69 mmol) was dissolved in anhydrous THF. N-methylmorpholine (0.84 mL, 7.69 mmol) was added to the solution. The reaction mixture was then cooled down to −15° C. and stirred for 5 min. Isobutylchloroformate (1.00, 7.69 mmol) was added and the mixture was stirred for 10 min at −15° C. O-tritylhydroxylamine (2.11 g, 7.69 mmol) was added followed by 2 more equivalents of N-methylmorpholine. Stirring continued for 15 min at −15° C. and 2 h at room temperature. Afterwards the mixture was poured into 2M HCl and extracted 3 times in each case with water, sodium bicarbonate solution (5%) and water. After washing with brine and drying over $Na_2SO_4$, solvent was evaporated in vacuo to yield 2.78 mg (90%) of 14 as a white solid with no further purification required. $^1$H NMR (DMSO-$d_6$, 400 MHz) δ 1.17-1.25 (4H, m), 1.79 (2H, t, J=5.8 Hz), 3.15 (2H, t, J=6.1 Hz), 7.27-7.31 (15H, m), 10.22 (1H, s); $^{13}$C NMR ($CDCl_3$, 100 MHz) δ 20.1, 27.7, 30.1, 50.6, 93.0, 127.8, 128.6, 140.6, 176.0.

6-Azido-O-tritylhexahydroxamate (15)

(As described in Mwakwari, S.C.; Guerrant, W.; Patil, V.; Khan, S. I.; Tekwani, B. L.; Gurard-Levin, Z. A.; Mrksich, M.; Oyelere, A. K. Nonpeptide Macrocyclic Histone Deacetylase (HDAC) Inhibitors Derived from Tricyclic Ketolide. *J. Med. Chem.* 2010, 53, 6100-6111)

7-Azido-O-tritylheptahydroxamate (16)

Reaction of 7-azidoheptanoic acid 10 (434 mg, 2.54 mmol) and O-tritylhydroxylamine (700 mg, 2.545 mmol) as described for the synthesis of 14, followed by flash chromatography (eluent 2:1 hexanes/EtOAc) gave 837 mg (77%) of 16 as a white solid. $^1$H NMR (DMSO-$d_6$, 400 MHz) δ 0.94-1.01 (2H, m), 1.06-1.19 (4H, m), 1.71-1.78 (4H, m), 3.59 (1H, s), 4.34 (2H, t, J=8), 7.25-7.36 (16H, m), 7.44-7.47 (1H, m), 8.07 (1H, s), 8.17-8.20 (1H, m), 8.51-8.52 (1H, m), 8.68 (1H, s), 9.03-9.04 (1H, m), 10.16 (1H, s); $^{13}C$ NMR ($CDCl_3$, 100 MHz) δ 25.8, 29.7, 30.7, 46.9, 50.1, 53.8, 93.1, 119.8, 123.5, 126.6, 127.7, 128.4, 128.8, 132.7, 144.0, 144.4, 146.7, 148.9, 176.8.

8-Azido-O-trityloctahydroxamate (17)

Reaction of 8-azidooctanoic acid 11 (1.71 g, 9.21 mmol) and O-tritylhydroxylamine (2.55 g, 9.27 mmol) as described for the synthesis of 14, followed by flash chromatography (eluent 2:1 hexanes/EtOAc) gave 2.59 g (88%) of 17 as a white solid. $^{1}H$ NMR ($CDCl_3$, 400 MHz) δ 0.88-1.39 (8H, m), 1.39-1.54 (4H, m), 3.12 (2H, t, J=6.9 Hz), 7.10-7.49 (15H, m), 7.67 (1H, s); $^{13}C$ NMR ($CDCl_3$, 100 MHz) δ 23.2, 24.9, 26.4, 28.7, 31.1, 33.2, 51.3, 93.1, 127.1, 128.0, 128.9, 141.0, 141.8, 146.8, 177.1.

9-Azido-O-tritylnonahydroxamate (18)

Reaction of 9-azidononanoic acid 12 (724 mg, 3.63 mmol) and O-tritylhydroxylamine (1.00 g, 3.63 mmol) overnight as described for the synthesis of 14, followed by flash chromatography (eluent 2:1 hexanes/EtOAc) gave 940 mg (56%) of 18 as a sticky white solid. $^{1}H$ NMR ($CDCl_3$, 400 MHz) δ 1.26 (10H, m), 1.57 (4H, m), 3.24 (2H, t, J=6.8 Hz), 7.34 (15H, m), 7.74 (1H, s).

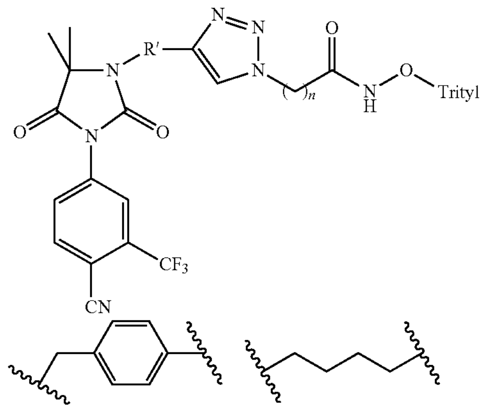

R′ =

19, n = 3
20, n = 4
21, n = 5
22, n = 6
23, n = 7
24, n = 8

25, n = 3
26, n = 4
27, n = 5
28, n = 6
29, n = 7
30, n = 8

Representative procedure for Cu(I)-catalyzed cycloaddition reaction. O-trityl-cyanonilutamide-benzyl-triazolylbutylhydroxamate (19)

4-[3-[(4-ethynylphenyl)methyl]-4,4-dimethyl-2,5-dioxo-1-imidazolidinyl]-2-(trifluoromethyl)-benzonitrile 4 (147.3 mg, 0.358 mmol), 4-azido-O-tritylbutylhydroxamate 13 (167 mg, 0.430 mmol) and DIPEA (94.35 mg, 0.730 mmol) were added to 2.55 mL anhydrous DMSO under argon. Copper(I) iodide (34.8 mg, 0.183 mmol) was then added, and reaction stirred under argon at ambient temperature overnight. The reaction mixture was diluted with DCM (30 mL) and washed with 1:4 $NH_4OH$/saturated $NH_4Cl$ (3×30 mL) and saturated $NH_4Cl$ (30 mL), and organic layer was dried over sodium sulfate, filtered and concentrated in vacuo. Column chromatography (eluent 80:4:1 DCM/Acetone/Methanol) gave 19 as a white solid (216 mg, 76%). $^{1}H$ NMR (400 MHz, DMSO-$d_6$) δ 1.39 (6H, s), 1.69-1.90 (4H, m), 4.00-4.17 (2H, m), 4.63 (2H, s), 7.22-7.43 (15H, m), 7.50 (2H, d, J=8.1 Hz), 7.78 (2H, d, J=8.1 Hz), 8.09 (1H, d, J=8.4 Hz), 8.24 (1H, s), 8.32 (1H, d, J=8.4 Hz), 8.37 (1H, s), 10.30 (1H, s) ppm.

O-trityl-cyanonilutamide-benzyl-triazolylpentahydroxamate (20)

Reaction of 4 and 14 as described for 19 gave the product 20 in 41% yield. $^{1}H$ NMR (400 MHz, $CDCl_3$) δ 1.24 (2H, s), 1.41 (6H, s), 1.49-1.75 (4H, m), 4.13-4.26 (2H, m), 4.63 (2H, s), 7.15-7.49 (15H, m), 7.41 (2H, d, J=8.0 Hz), 7.74 (1H, s), 7.79 (2H, d, J=7.9 Hz), 7.89 (1H, d, J=8.4 Hz), 8.03 (1H, dd, J=1.7, 8.5 Hz), 8.19 (1H, d, J=1.4 Hz) ppm.

O-trityl-cyanonilutamide-benzyl-triazolylhexahydroxamate (21)

Reaction of 4 and 15 as described for 19 gave the product 21 in 98% yield. $^{1}H$ NMR (400 MHz, $CDCl_3$) δ 0.91-1.15 (2H, m), 1.18-1.33 (2H, m), 1.40 (6H, s), 1.50-1.63 (2H, m), 1.66-1.81 (3H, m), 4.18-4.33 (2H, m), 4.63 (2H, s), 7.34 (15H, dd, J=9.1, 55.1 Hz), 7.41 (2H, d, J=7.2 Hz), 7.76 (1H, s), 7.80 (2H, d, J=8.1 Hz), 7.83 (1H, s), 7.88 (1H, d, J=8.4 Hz), 8.02 (1H, dd, J=1.7, 8.4 Hz), 8.18 (1H, d, J=1.6 Hz) ppm.

O-trityl-cyanonilutamide-benzyl-triazolylheptahydroxamate (22)

Reaction of 4 and 16 as described for 19 gave the product 22 in 82% yield. $^{1}H$ NMR (400 MHz, $CDCl_3$) δ 0.97-1.32 (6H, m), 1.42 (6H, s), 1.75-1.95 (4H, m), 4.32 (2H, s), 4.64 (2H, s), 7.35 (15H, dd, J=14.2, 54.1 Hz), 7.42 (2H, d, J=8.1 Hz), 7.74 (1H, s), 7.81 (2H, d, J=8.1 Hz), 7.90 (1H, d, J=8.5 Hz), 8.04 (1H, dd, J=1.8, 8.4 Hz), 8.19 (1H, s) ppm.

O-trityl-cyanonilutamide-benzyl-triazolyloctahydroxamate (23)

Reaction of 4 and 17 as described for 19 gave the product 23 in 92% yield. $^{1}H$ NMR ($CDCl_3$, 400 MHz) δ 1.03 (2H, m), 1.23 (6H, m), 1.42 (6H, s), 1.56 (2H, m), 1.87 (2H, m), 4.35 (2H, t, J=7.1), 4.65 (2H, s), 7.32 (15H, m), 7.42 (2H, d, J=8.2), 7.61 (1H, s), 7.76 (1H, s), 7.82 (2H, d, J=8.2), 7.91 (1H, d, J=8.4), 8.04 (1H, dd, J=1.8, 8.4), 8.19 (1H, d, J=1.7).

O-trityl-cyanonilutamide-benzyl-triazolylnonahydroxamate (24)

Reaction of 4 and 18 as described for 19 gave the product 24 in 87% yield. $^{1}H$ NMR (300 MHz, $CDCl_3$) 0.88-1.34 (11H, m), 1.42 (6H, s), 1.47-1.65 (2H, m), 1.74-1.95 (3H, m), 4.35 (2H, t, J=7.1 Hz), 4.64 (2H, s), 7.35 (15H, dd, J=12.0, 40.9 Hz), 7.42 (2H, d, J=8.4 Hz), 7.77 (1H, s), 7.82 (2H, d, J=8.3 Hz), 7.90 (1H, d, J=8.5 Hz), 8.04 (1H, dd, J=2.0, 8.4 Hz), 8.19 (1H, d, J=2.0 Hz) ppm.

O-trityl-cyanonilutamide-butyl-triazolylbutylhydroxamate (25)

Reaction of 5 and 13 as described for 19 gave the product 25 in 87% yield. $^{1}11$ NMR (400 MHz, DMSO-$d_6$) 1.43 (6H, s), 1.58-1.73 (6H, m), 1.73-1.85 (2H, m), 2.62 (2H, t, J=6.9 Hz), 3.99 (2H, t, J=6.8 Hz), 7.10-7.40 (15H, m), 7.66 (1H, s), 8.01 (1H, dd, J=2.0, 8.4 Hz), 8.17 (1H, d, J=1.8 Hz), 8.28 (1H, d, J=8.4 Hz), 10.29 (1H, s) ppm.

O-trityl-cyanonilutamide-butyl-triazolylpentahydroxamate (26)

Reaction of 5 and 14 as described for 19 gave the product 26 in 93% yield. $^1$H NMR (400 MHz, $CDCl_3$) δ 1.15-1.29 (2H, m), 1.50 (6H, s), 1.52-1.67 (4H, m), 1.69-1.80 (4H, m), 2.75 (2H, t, J=6.8 Hz), 3.37 (2H, t, J=7.2 Hz), 4.13 (2H, t, J=6.7 Hz), 7.24 (1H, s), 7.25-7.50 (15H, m), 7.78 (1H, s), 7.88 (1H, d, J=8.4 Hz), 7.98 (1H, dd, J=1.9, 8.5 Hz), 8.14 (1H, d, J=1.7 Hz) ppm.

O-trityl-cyanonilutamide-butyl-triazolylhexahydroxamate (27)

Reaction of 5 and 15 as described for 19 gave the product 27 in 84% yield. $^1$H NMR (400 MHz, $CDCl_3$) δ 0.93-1.16 (2H, m), 1.18-1.33 (2H, m), 1.50 (6H, s), 1.63-1.95 (8H, m), 2.72-2.79 (2H, m), 3.32-3.41 (2H, m), 4.20 (2H, t, J=7.1 Hz), 7.14-7.53 (15H, m), 7.77 (1H, s), 7.87 (1H, d, J=8.5 Hz), 7.98 (1H, dd, J=1.7, 8.5 Hz), 8.14 (1H, d, J=1.7 Hz) ppm.

O-trityl-cyanonilutamide-butyl-triazolylheptahydroxamate (28)

Reaction of 5 and 16 as described for 19 gave the product 28 in 82% yield. $^1$H NMR (400 MHz, DMSO-$d_6$) δ 0.87-0.97 (2H, m), 0.97-1.07 (2H, m), 1.08-1.18 (2H, m), 1.42 (6H, s), 1.55-1.69 (6H, m), 1.73 (2H, t, J=7.2 Hz), 2.57-2.68 (2H, m), 3.27-3.36 (2H, m), 4.20 (2H, t, J=7.1 Hz), 7.18-7.39 (15H, m), 7.81 (1H, s), 8.01 (1H, dd, J=2.0, 8.4 Hz), 8.17 (1H, d, J=1.7 Hz), 8.28 (1H, d, J=8.4 Hz), 10.15 (1H, s) ppm.

O-trityl-cyanonilutamide-butyl-triazolyloctahydroxamate (29)

Reaction of 5 and 17 as described for 19 gave the product 29 in 92% yield. $^1$H NMR ($CDCl_3$, 400 MHz) δ 1.08 (8H, m), 1.49 (6H, s), 1.54 (2H, m), 1.77 (6H, m), 2.75 (2H, s), 3.37 (2H, s), 4.25 (2H, t, J=7.17, 7.17), 7.31 (15H, s), 7.61 (1H, s), 7.76 (1H, s), 7.87 (1H, d, J=8.4), 7.97 (1H, dd, J=1.8, 8.4), 8.13 (1H, d, J=1.5).

O-trityl-cyanonilutamide-butyl-triazolylnonahydroxamate (30)

Reaction of 5 and 18 as described for 19 gave the product 30 in 95% yield. $^1$H NMR (300 MHz, $CDCl_3$) δ 0.91-1.42 (12H, m), 1.49 (6H, s), 1.67-1.87 (6H, m), 2.75 (2H, s), 3.36 (2H, s), 4.26 (2H, t, J=7.1 Hz), 7.30 (15H, s), 7.76 (1H, s), 7.86 (1H, d, J=8.4 Hz), 7.98 (1H, dd, J=1.7, 8.4 Hz), 8.13 (1H, d, J=1.2 Hz) ppm.

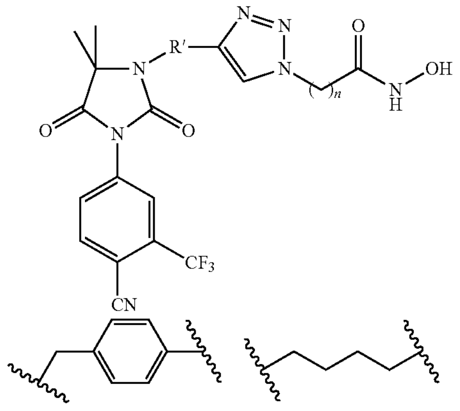

R' =

| | |
|---|---|
| 31, n = 3 | 37, n = 3 |
| 32, n = 4 | 38, n = 4 |
| 33, n = 5 | 39, n = 5 |
| 34, n = 6 | 40, n = 6 |
| 35, n = 7 | 41, n = 7 |
| 36, n = 8 | 42, n = 8 |

Representative Procedure for Deprotection of O-Trityl-Hydroxamates. O-trityl-cyanonilutamide-benzyl-triazolylbutylhydroxamic acid (31)

O-trityl-cyanonilutamide-benzyl-triazolylbutylhydroxamate 19 (195 mg, 0.243 mmol) was dissolved in 9.1 mL of DCM and 0.2 mL triisopropylsilane at ambient temperature. Trifluoroacetic acid (0.18 mL) was added, and then triisopropylsilane was added dropwise until solution turned from yellow to clear, and reaction was stirred for 5 minutes. Solvent and trifluoroacetic acid were removed in vacuo, and residue was washed with 10 mL of petroleum ether. Preperative TLC (eluent 37:1 acetonitile/water) provided 96 mg (71%) of 31 as a light yellow semisolid. $^1$H NMR (DMSO-$d_6$, 400 MHz) δ 1.38 (6H, s), 1.85-2.19 (4H, m), 4.27-4.49 (2H, m), 4.62 (2H, s), 7.50 (2H, d, J=7.2 Hz), 7.80 (2H, d, J=6.8 Hz), 8.08 (1H, d, J=7.1 Hz), 8.23 (1H, s), 8.30 (1H, d, J=7.0 Hz), 8.57 (1H, s), 10.52 (1H, s) ppm.

O-trityl-cyanonilutamide-benzyl-triazolylpentahydroxamic acid (32)

Reaction of 20 with trifluoroacetic acid as described for 31 gave the product 32 in 63% yield. HRMS (MALDI) calculated for $[C_{27}H_{26}F_3N_7O_4+H]^+$570.2032. found 570.21.

O-trityl-cyanonilutamide-benzyl-triazolylheptahydroxamic acid (33)

Reaction of 21 with trifluoroacetic acid as described for 31 gave the product 33 in 16% yield. HRMS (MALDI) calculated for $[C_{28}H_{28}F_3N_7O_4+H]^+$584.2188. found 584.2217.

O-trityl-cyanonilutamide-benzyl-triazolylhexahydroxamic acid (34)

Reaction of 22 with trifluoroacetic acid as described for 31 gave the product 34 in 67% yield. HRMS (MALDI) calculated for $[C_{29}H_{30}F_3N_7O_4+H]^+$598.2345. found 598.2395.

O-trityl-cyanonilutamide-benzyl-triazolylheptahydroxamic acid (35)

Reaction of 23 with trifluoroacetic acid as described for 31 gave the product 35 in 35% yield. HRMS (MALDI) calculated for $[C_{30}H_{32}F_3N_7O_4+H]^+$612.2501. found 612.2524.

O-trityl-cyanonilutamide-benzyl-triazolyloctahydroxamic acid (36)

Reaction of 24 with trifluoroacetic acid as described for 31 gave the product 36 in 92% yield. $^1H$ NMR (400 MHz, $CDCl_3$) δ 0.63-1.32 (10H, m), 1.39 (6H, s), 1.45-1.68 (2H, m), 1.72-2.00 (2H, m), 4.34 (2H, bs), 4.60 (2H, s), 7.39 (2H, bs), 7.68-7.84 (2H, m), 7.90 (1H, d, J=6.4 Hz), 7.99 (1H, d, J=6.7 Hz), 8.13 (1H, s) ppm.

O-trityl-cyanonilutamide-butyl-triazolylbutylhydroxamic acid (37)

Reaction of 25 with trifluoroacetic acid as described for 31 gave the product 37 in 100% yield. $^1H$ NMR (400 MHz, DMSO-$d_6$) δ 1.32-1.52 (6H, m), 1.65 (4H, s), 1.97 (4H, s), 2.65 (2H, s), 3.34 (2H, s), 4.29 (2H, d, J=6.1 Hz), 7.86 (1H, s), 8.03 (1H, d, J=8.2 Hz), 8.18 (1H, s), 8.30 (1H, d, J=8.3 Hz), 10.47 (1H, s) ppm.

O-trityl-cyanonilutamide-butyl-triazolylpentahydroxamic acid (38)

Reaction of 26 with trifluoroacetic acid as described for 31 gave the product 38 in 28% yield. HRMS (MALDI) calculated for $[C_{24}H_{28}F_3N_7O_4+H]^+$536.2188. found 536.2230.

O-trityl-cyanonilutamide-butyl-triazolylheptahydroxamic acid (39)

Reaction of 27 with trifluoroacetic acid as described for 31 gave the product 39 in 38% yield. HRMS (MALDI) calculated for $[C_{25}H_{30}F_3N_7O_4+H]^+$550.2345. found 550.2383.

O-trityl-cyanonilutamide-butyl-triazolylhexhydroxamic acid (40)

Reaction of 28 with trifluoroacetic acid as described for 31 gave the product 40 in 38% yield. HRMS (MALDI) calculated for $[C_{26}H_{32}F_3N_7O_4+H]^+$564.2501. found 564.2596.

O-trityl-cyanonilutamide-butyl-triazolylheptahydroxamic acid (41)

Reaction of 29 with trifluoroacetic acid as described for 31 gave the product 41 in 49% yield. HRMS (MALDI) calculated for $[C_{27}H_{34}F_3N_7O_4+H]^+$578.2658. found 578.2678.

O-trityl-cyanonilutamide-butyl-triazolyloctahydroxamic acid (42)

Reaction of 30 with trifluoroacetic acid as described for 31 gave the product 42 in 75% yield. $^1H$ NMR (400 MHz, $CDCl_3$) δ 0.73-1.40 (10H, m), 1.48 (6H, s), 1.52-1.62 (2H, m), 1.64-1.95 (6H, m), 2.05-2.20 (2H, m), 3.34 (2H, bs), 4.29 (2H, bs), 7.89 (1H, s), 7.95 (1H, s), 8.09 (1H, s) ppm.

Additional Synthesis:

Additional active compounds of the present invention are synthesized in accordance with Scheme 2 below:

SCHEME 2

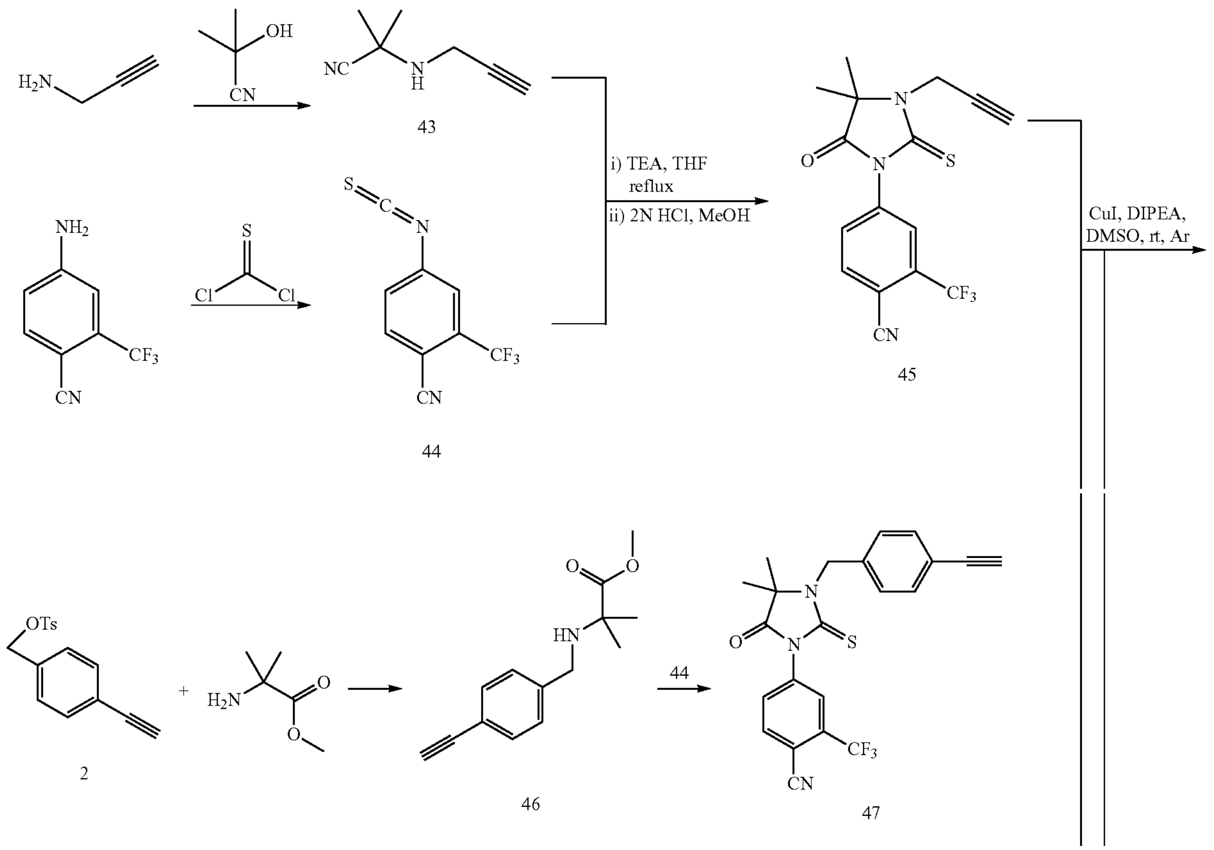

43
44
45
2
46
47

-continued
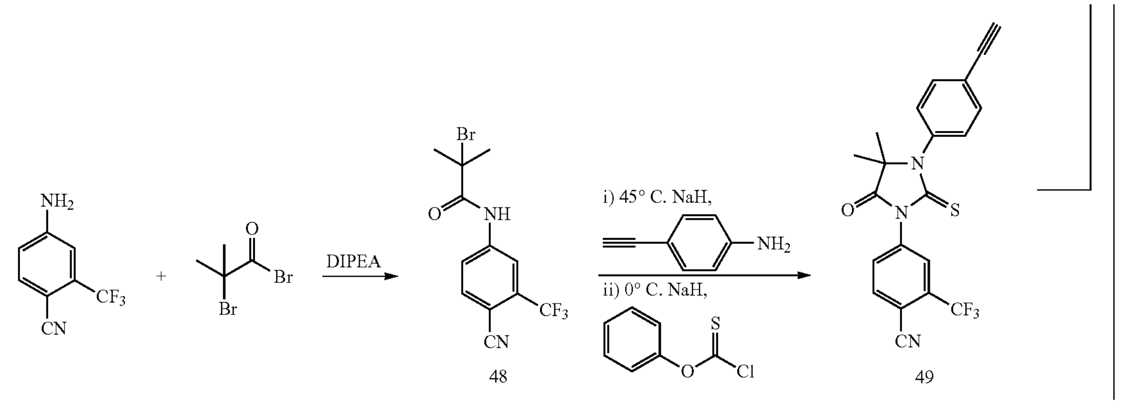
48
49
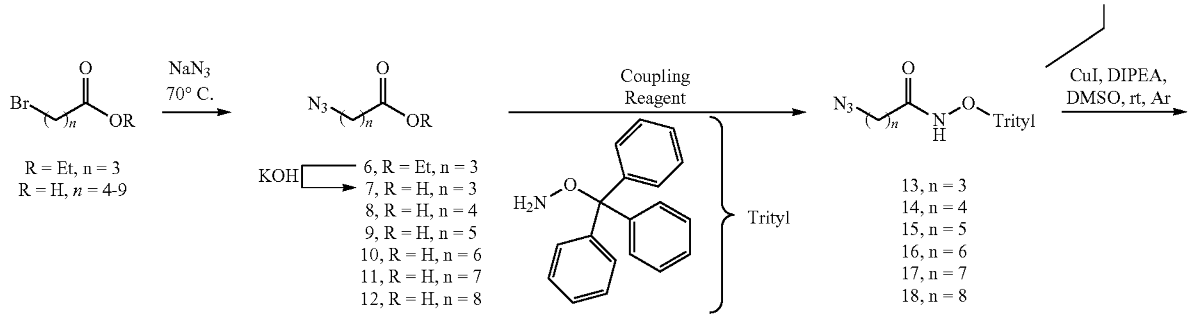
R = Et, n = 3
R = H, n = 4-9
6, R = Et, n = 3
7, R = H, n = 3
8, R = H, n = 4
9, R = H, n = 5
10, R = H, n = 6
11, R = H, n = 7
12, R = H, n = 8
13, n = 3
14, n = 4
15, n = 5
16, n = 6
17, n = 7
18, n = 8
PANEL 1 of 2
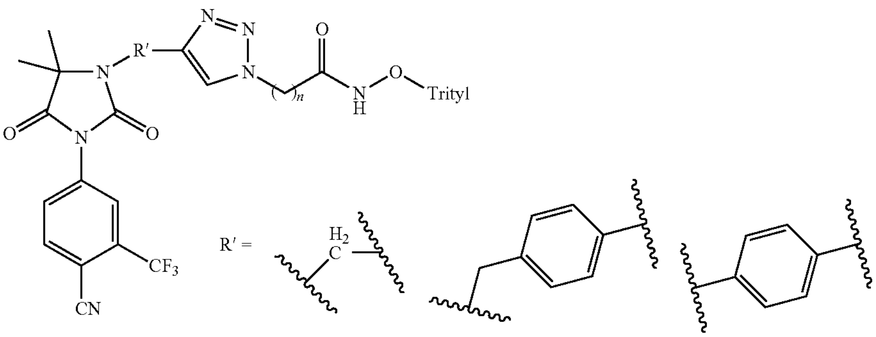
50, n = 3
51, n = 4
52, n = 5
53, n = 6
54, n = 7
55, n = 8
56, n = 3
57, n = 4
58, n = 5
59, n = 6
60, n = 7
61, n = 8
62, n = 3
63, n = 4
64, n = 5
65, n = 6
66, n = 7
67, n = 8
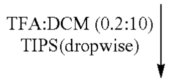

-continued

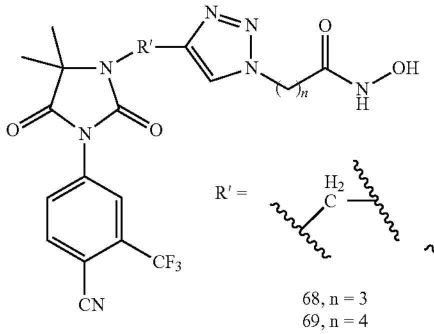

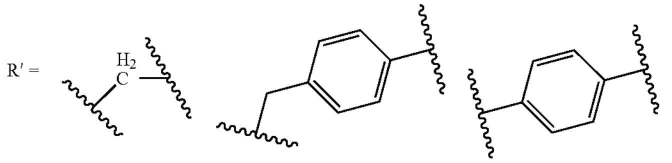

68, n = 3
69, n = 4
70, n = 5
71, n = 6
72, n = 7
73, n = 8

74, n = 3
75, n = 4
76, n = 5
77, n = 6
78, n = 7
79, n = 8

80, n = 3
81, n = 4
82, n = 5
83, n = 6
84, n = 7
85, n = 8

PANEL 2 OF 2

Biological Activity.

Antiproliferative assays and In vitro binding assays were performed on the following compounds:

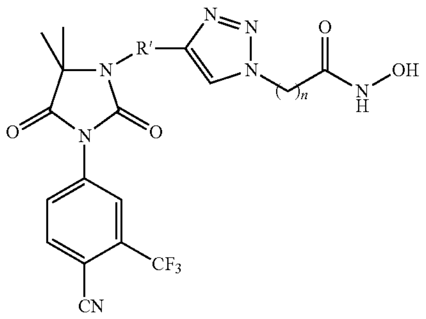

Aryl Nil.

Alkyll Nil.

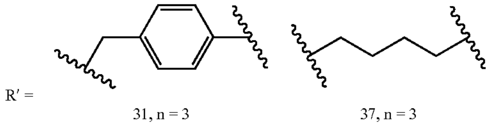

31, n = 3
32, n = 4
33, n = 5
34, n = 6
35, n = 7
36, n = 8

37, n = 3
38, n = 4
39, n = 5
40, n = 6
41, n = 7
42, n = 8

Figure 3A:
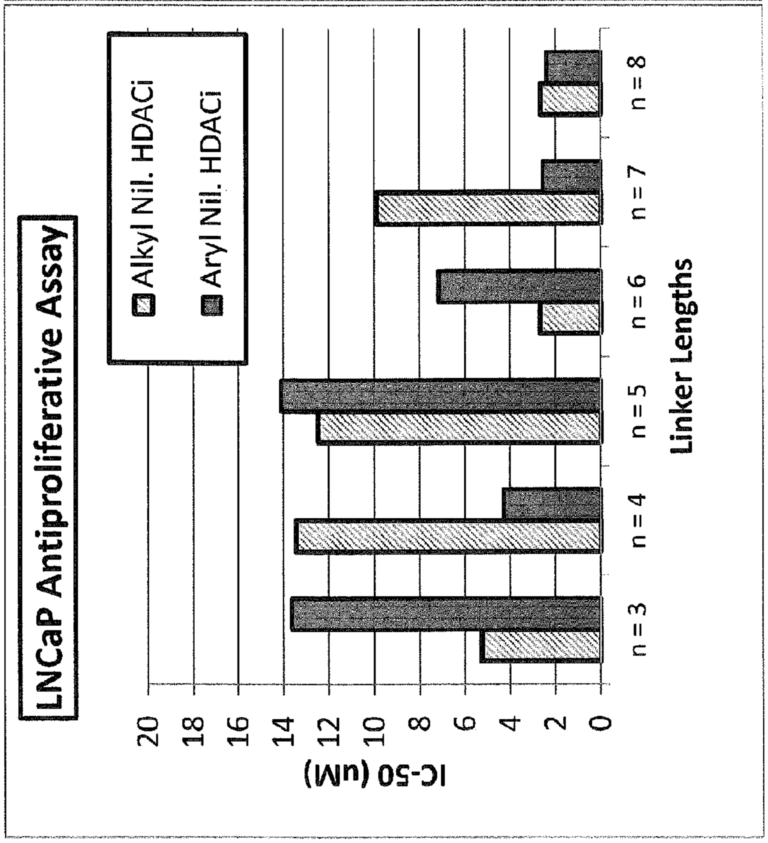
FIGS. 3A-3B show antiproliferative assays were performed on low passage cells for a 72 hour drug incubation period, and read using colorimetric assays with 0.4% DMSO control. *Greater than 50 μM
Figure 3B:
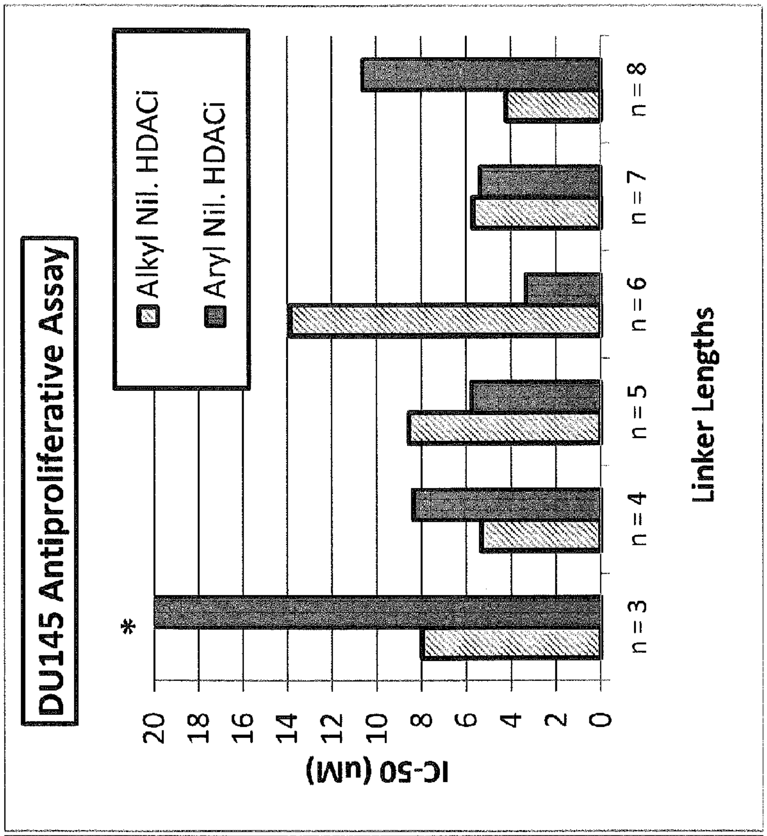

Antiproliferative assays were performed on low passage cells for a 72 hour drug incubation period, and read using colorimetric assays with 0.4% DMSO control. Data is given in FIGS. 3A-3B (*Greater than 50 μM IC-50.).

Figure 4:
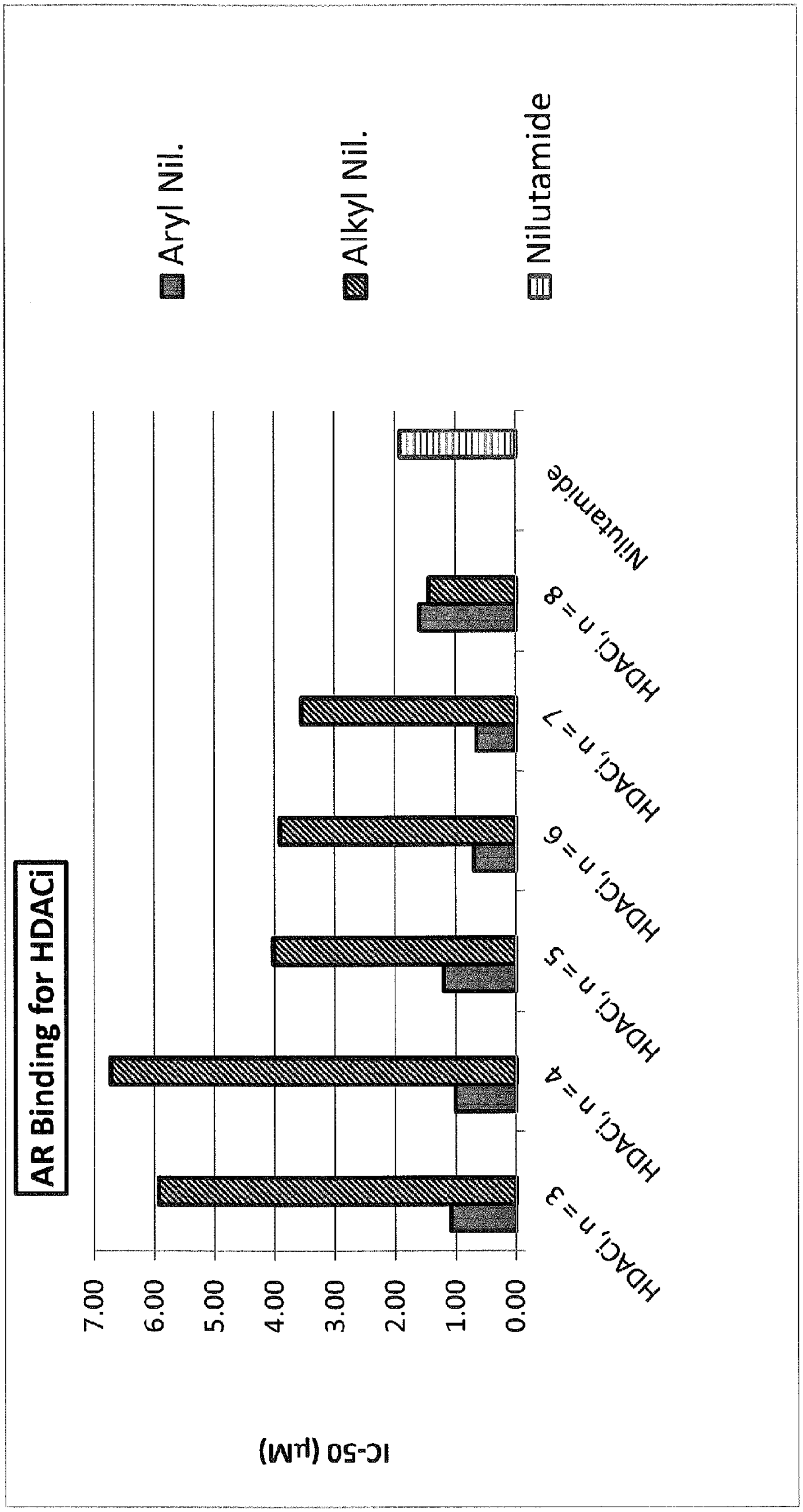
FIG. 4 shows In vitro adrenergic receptor (AR) binding. The phenyl head group (Aryl Nil. HDACi) and the alkyl head group (Alkyl Nil. HDACi) with various linkers (n=3-8), and Cyano-Nilutamide, were tested by competition against [$^3$H] Mibolerone in vitro in cytosolic rat AR. The improved binding with the Aryl cap group can be explained by π-π stacking with the AR surface and lower entropic penalties.

In vitro Androgen receptor (AR) binding is shown in FIG. 4. The phenyl head group (Aryl Nil. HDACi) and the alkyl head group (Alkyl Nil. HDACi) with various linkers (n=3-8), and Cyano-Nilutamide, were tested by competition against [$^3$H] Mibolerone in vitro in cytosolic rat AR.

We claim:

1. A compound of Formula I:

(I)

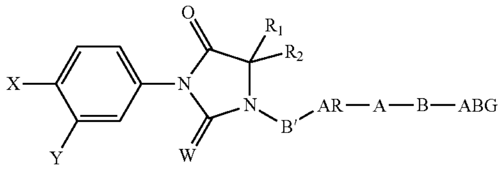

wherein:

AR is an aryl group or covalent bond;

B' is absent or consists of a $C_{1-6}$ group, optionally containing one or more heteroatoms, wherein the carbon atoms and/or heteroatoms are in a linear arrangement;

A is a linking group connected to AR, wherein A is selected from the group consisting of:

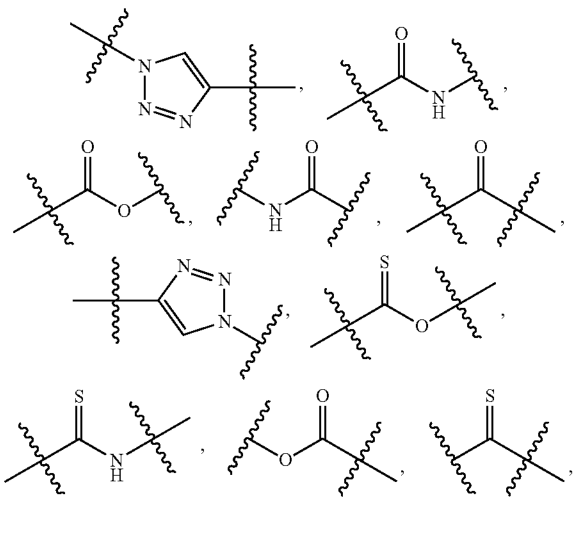

-continued

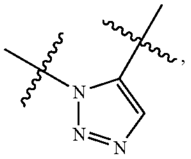, 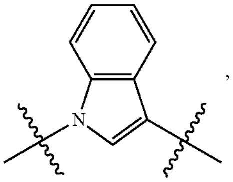,

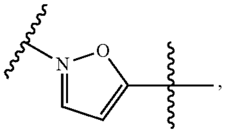, 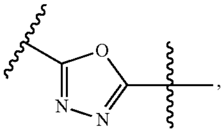,

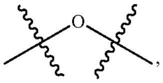, 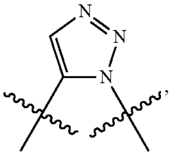,

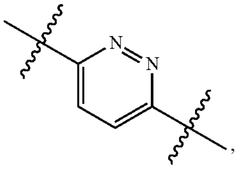, 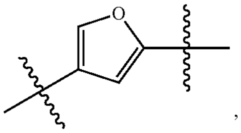,

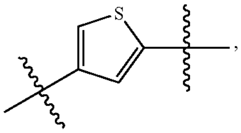, 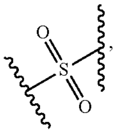,

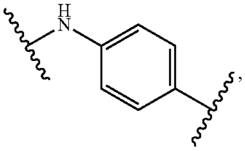, 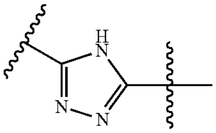,

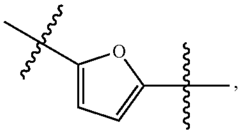, 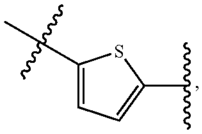, and

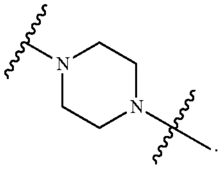.

B is $C_1$-$C_{11}$ linear alkyl optionally containing one or more double or triple bonds and/or —$CH_3$ and/or $CH_2CH_3$ branching;

ZBG is selected from the group consisting of

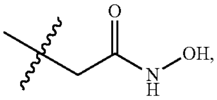 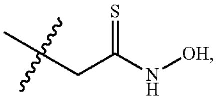

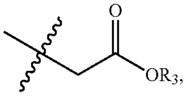 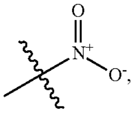 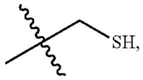

-continued

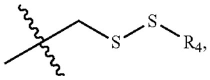 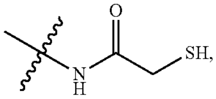

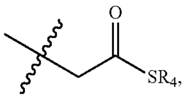 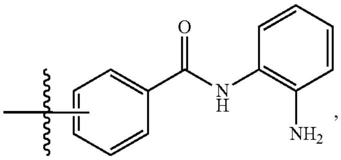,

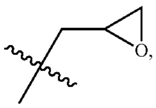 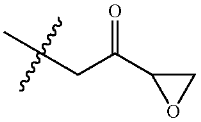,

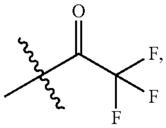 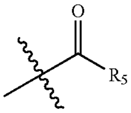, and

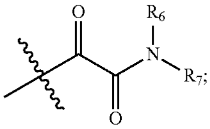

$R_1$ and $R_2$ are independently selected from of hydrogen or $C_1$ to $C_8$ alkyl or together form a group comprising 3-8 carbon atoms that is selected from cycloalkyl or substituted cycloalkyl;

$R_3$ is H or a salt counter ion;

$R_4$ is acyl or alkyl;

$R_5$ is alkyl; and $R_6$ and $R_7$ are independently H or alkyl;

W is selected from the group consisting of O and S;

X is selected from the group consisting of cyano and nitro;

Y is selected from the group consisting of trifluoromethyl and iodo;

or a pharmaceutically acceptable salt thereof.

2. The compound of claim 1, wherein B' is absent.

3. The compound of claim 1, wherein B' is C1 to C6 linear alkyl.

4. The compound of claim 1, wherein AR is a covalent bond.

5. The compound of claim 1, wherein AR is selected from the group consisting of:

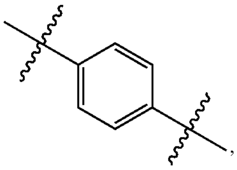, 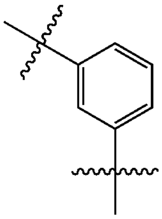,

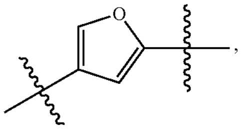, 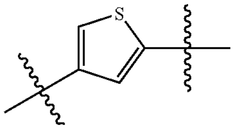,

-continued

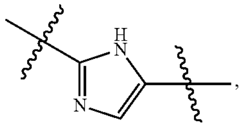,
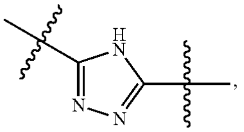,
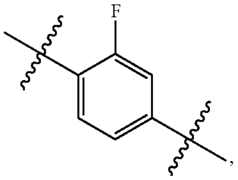,
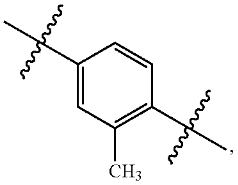,
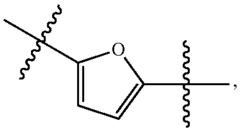,
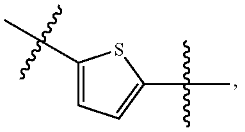,
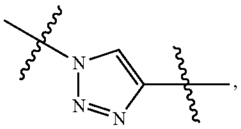,
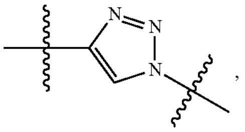,
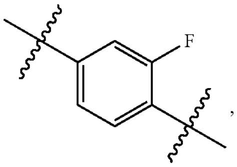,
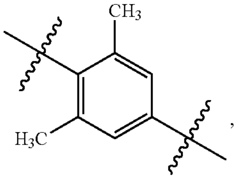,
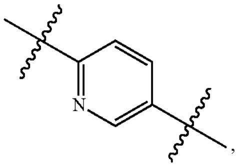,
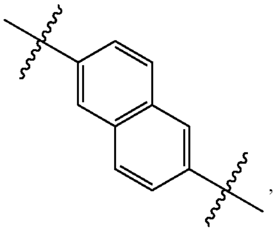,
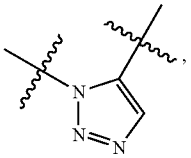,
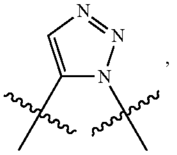,
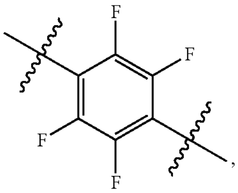,
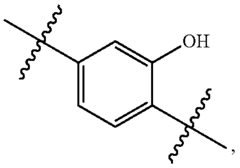,
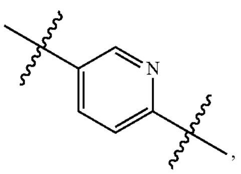,
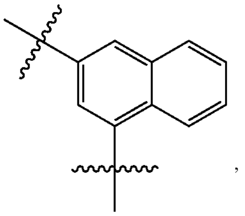, -continued

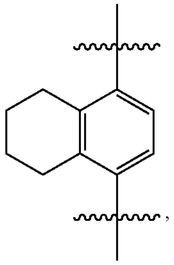,
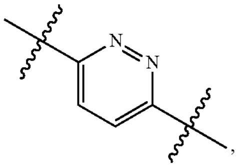,
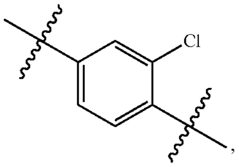,
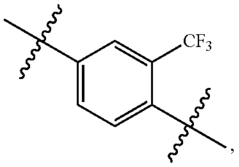,
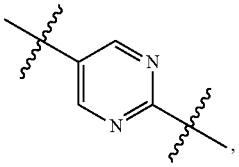,
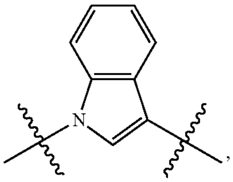,
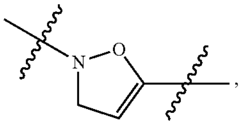,
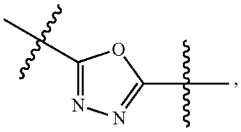,
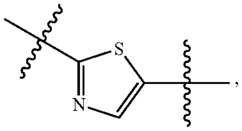,
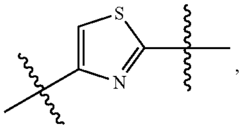, where

indicates optional connecting points to A and B', or to A and the nitrogen atom of the hydantoin group when B' is absent.

6. The compound of claim 1, wherein B is C1 to C8 linear alkyl.

7. The compound of claim 1, wherein $R_1$ and $R_2$ are each independently selected from the group consisting of H and C1 to C8 alkyl; or $R_1$ and $R_2$ together form a C3 to C8 cycloalkyl.

8. The compound of claim 1, wherein:

B' is present or absent, and when present is C1 to C6 linear alkyl;

AR is an aryl group or covalent bond, and when an aryl group, and when present is selected from the group consisting of:

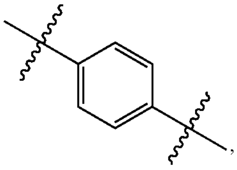,
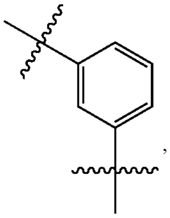,

-continued
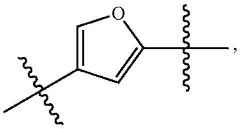, 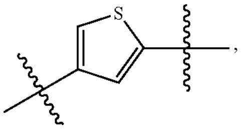,
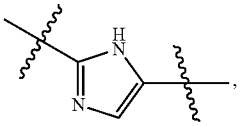, 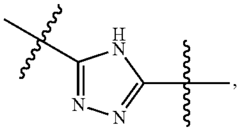,
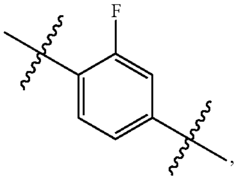, 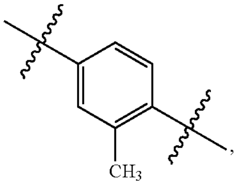,
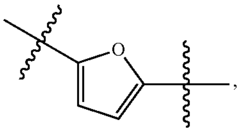, 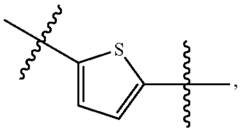,
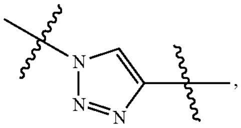, 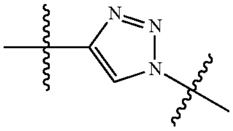,
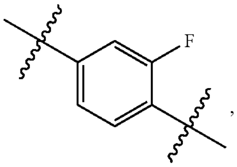, 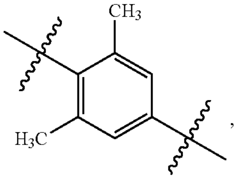,
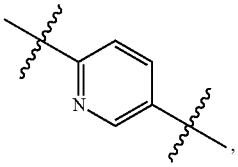, 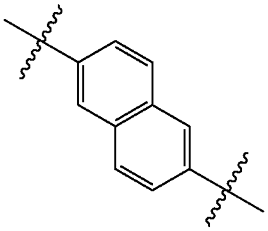,
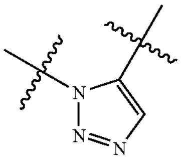, 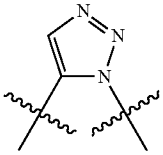,
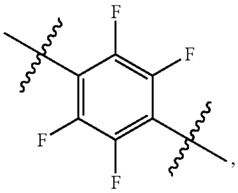, 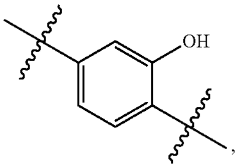,
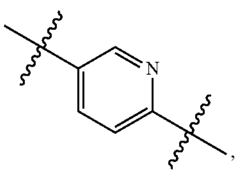, 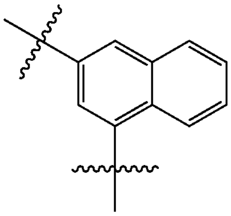,
-continued
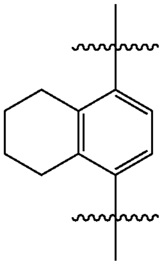, 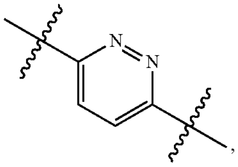,
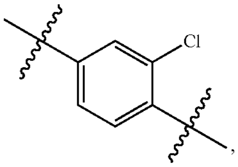, 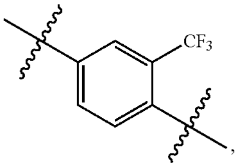,
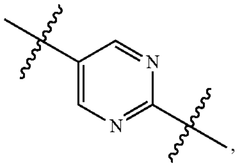, 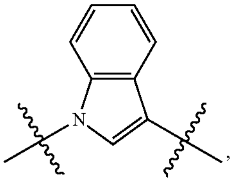,
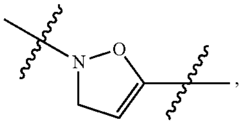, 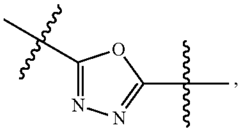,
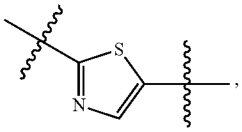, 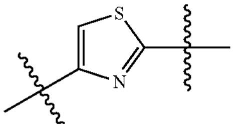,
where
indicates optional connecting points to A and B', or to A and the nitrogen atom of the hydantoin group when B' is absent;
A is selected from the group consisting of:
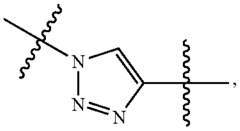, 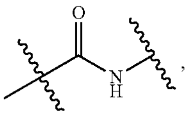,
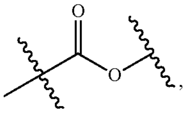, 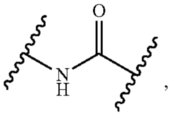, 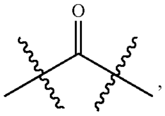, -continued

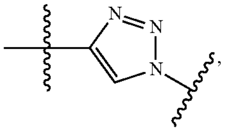, 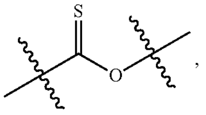,

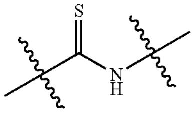, 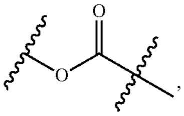, 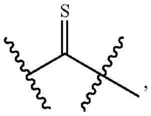,

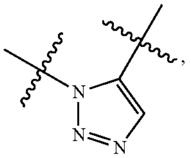, 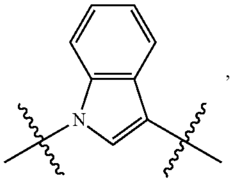,

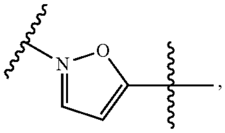, 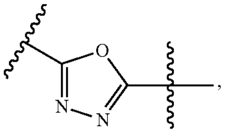,

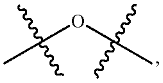, 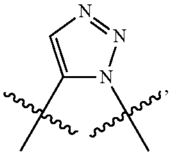,

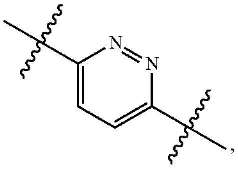, 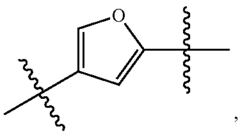,

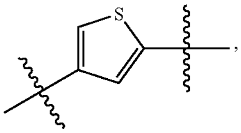, 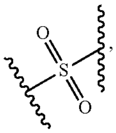,

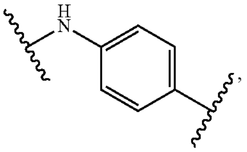, 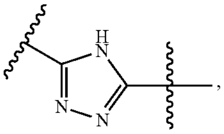,

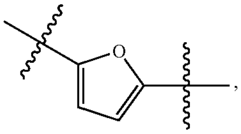, 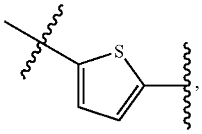, and

-continued

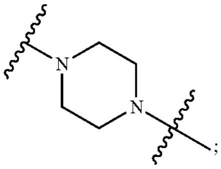;

B is C1 to C8 linear alkyl;

ZBG is selected from the group consisting of

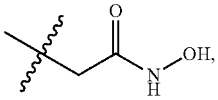, 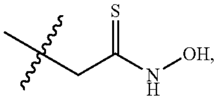,

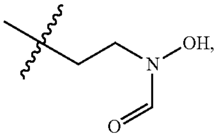, 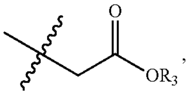,

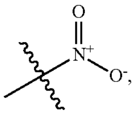, 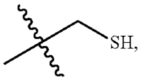, 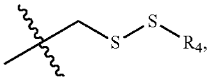,

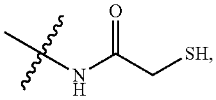, 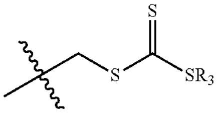,

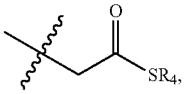, 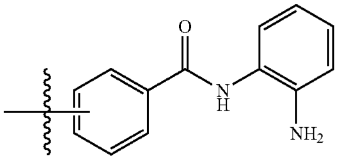,

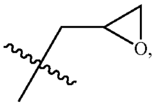, 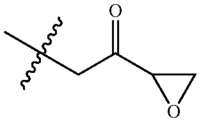,

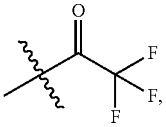, 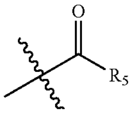 and

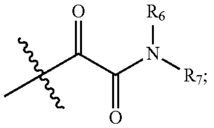;

$R_1$ and $R_2$ are each independently selected from the group consisting of H and C1 to C8 alkyl;

or $R_1$ and $R_2$ together form a C3 to C8 cycloalkyl;

$R_3$ is H or a salt counter ion;

$R_4$ is acyl or alkyl;

$R_5$ is alkyl; and $R_6$ and $R_7$ are independently H or alkyl.

9. The compound of claim 1 selected from the group consisting of:

31
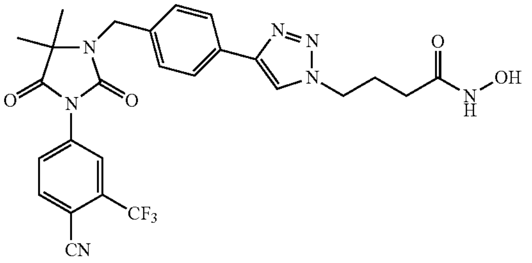
32
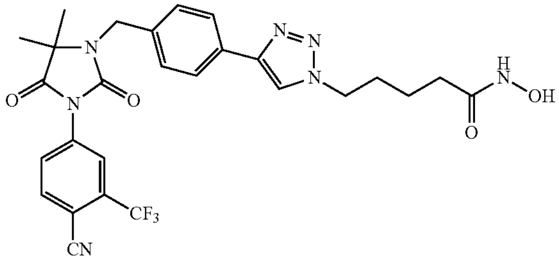
;
33
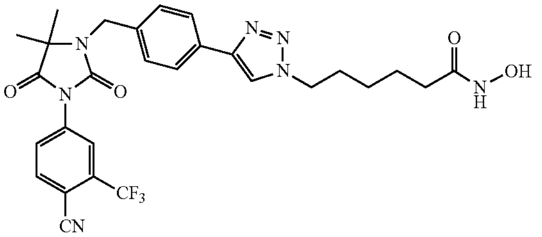
34
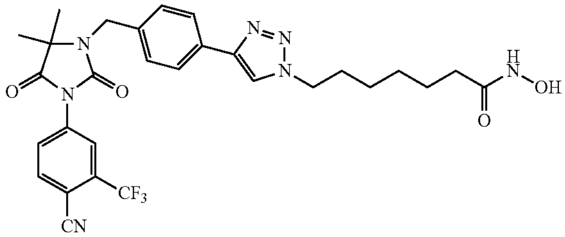
35
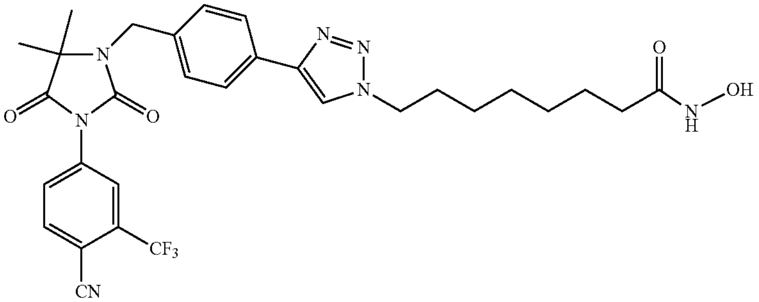
36
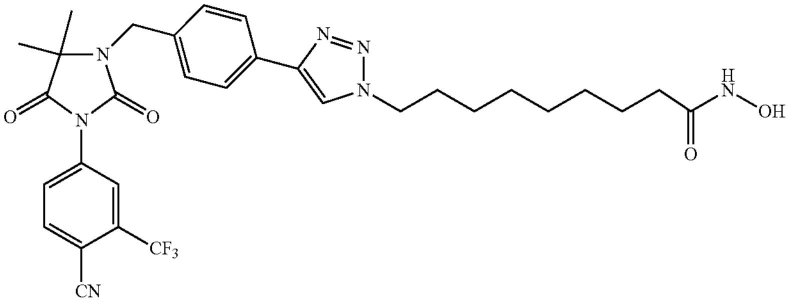
37
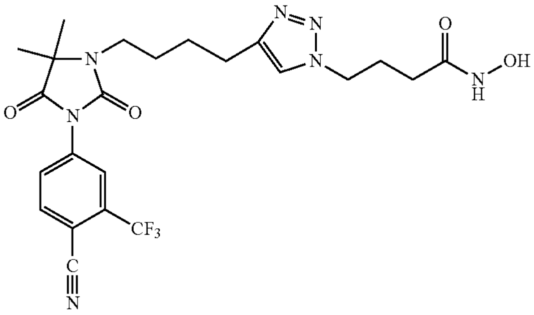
38
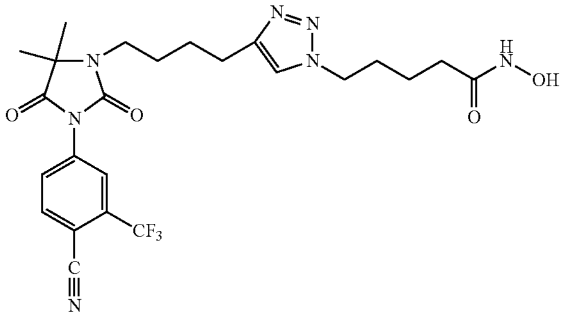

-continued

39

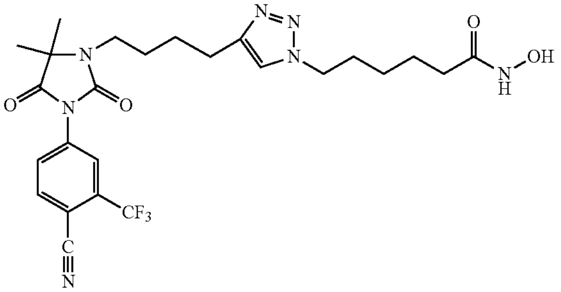

40

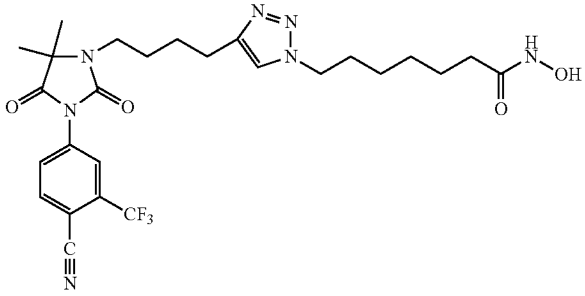

41

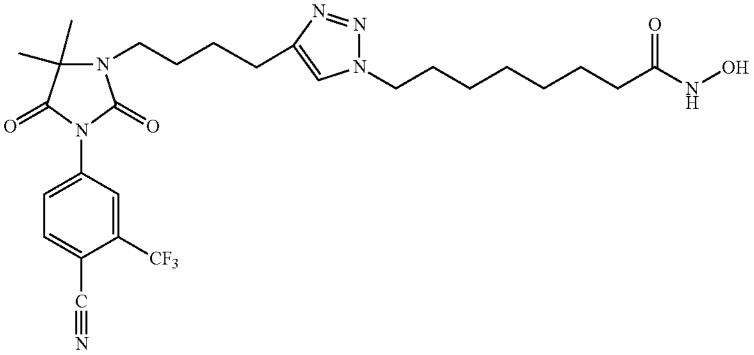 [SMILES: CC1(C)C(=O)N(c2ccc(C#N)c(C(F)(F)F)c2)C(=O)N1CCCCc1cn(CCCCCCCC(=O)NO)nn1]

42

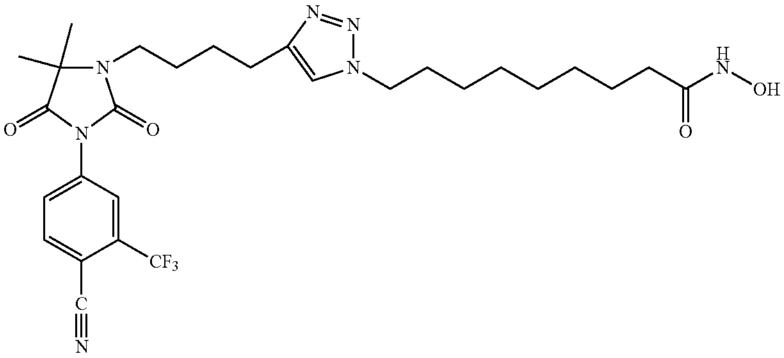 [SMILES: CC1(C)C(=O)N(c2ccc(C#N)c(C(F)(F)F)c2)C(=O)N1CCCCc1cn(CCCCCCCCC(=O)NO)nn1]

and pharmaceutically acceptable salts thereof.

10. The compound of claim 1, wherein ZBG is hydroxamic acid.

11. The compound of claim 1, wherein ZBG is hydroxamic acid and W is S.

12. A pharmaceutical composition comprising an effective amount of the compound of claim 1 in combination with a pharmaceutically acceptable diluent, excipient, or carrier.

13. A method of treating prostate cancer in a human or animal subject comprising administering said subject an effective amount of a compound of claim 1.

14. The method of claim 13, wherein ZBG is hydroxamic acid.

15. The method of claim 13, wherein and ZBG is hydroxamic acid and W is S.

16. The method of claim 13, wherein the prostate cancer is selected from hormone sensitive prostate cancer and hormone refractory prostate cancer.

17. The method of claim 13, wherein the compound is administered enterally or parenterally.

* * * * *

UNITED STATES PATENT AND TRADEMARK OFFICE
CERTIFICATE OF CORRECTION

PATENT NO. : 9,139,565 B2
APPLICATION NO. : 13/824661
DATED : September 22, 2015
INVENTOR(S) : Oyelere et al.

It is certified that error appears in the above-identified patent and that said Letters Patent is hereby corrected as shown below:

In the Specification:
Column 1, Line 67: Please correct "cancer (inj a, MJ.;" to read -- cancer (inja, M.J.; --

Column 4, Line 35: Please correct "50 μM" to read -- 50μM IC-50. --

Column 12, Lines 49 and 50: Please correct "-5-yl, 1,2,4-thiadiazol-5-yl,"
to read -- -5yl, 5oxo-1,2,4-oxadiazol-3-yl, 1,2,4-thiadiazol-3-yl, 1,2,4-thiadiazol-5-yl, --

Column 12, Line 51: Please correct "5-yl, 1,2,4-triazol-5-yl, 5-oxazolyl,"
to read -- 5-yl, 1,2,4-triazol-3-yl, 1,2,4-triazol-5-yl, 1,2,3,4-tetrazol-5-yl, 5-oxazolyl, --

Column 36, Line 65: Please correct "$^{1}$ 11 NMR (400 MHz, DMSO-$d_6$) 1.43"
to read -- $^{1}$H NMR (400 MHz, DMSO-$d_6$) δ --

In the Claims:
Column 44, Claim 1, Line 30: Please correct the Formula below:

" 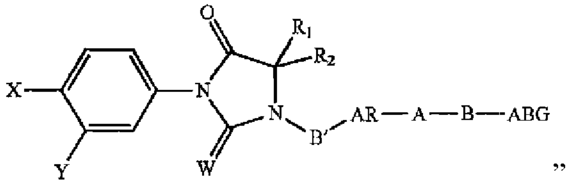 "

to read as:

-- 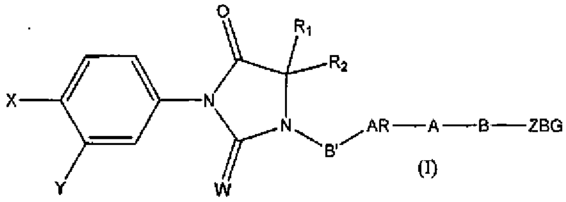 (I) --

Signed and Sealed this
Fifth Day of July, 2016

Michelle K. Lee
*Director of the United States Patent and Trademark Office*

Column 45, Claim 1, Line 50: Please change the "." at the end of the compound to a -- ; --

Column 46, Claim 1, Line 10: Please add the compound below at the beginning of Line 10:

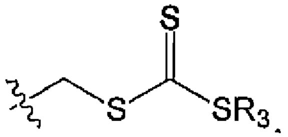

Column 46, Claim 1, Line 28: Please correct "from of hydrogen" to read -- from hydrogen --

Column 48, Claim 8, Lines 54-56: Please correct "AR is an aryl group or covalent bond, and when an aryl group, and when present is selected from the group consisting of:"

to read -- AR is an aryl group or covalent bond, and when an aryl group is present it is selected from the group consisting of: --

Column 52, Claim 8, Line 20: Please delete the compound below:

" 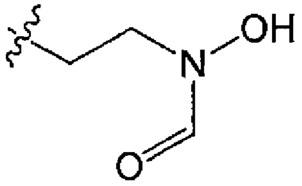 "

Column 54, Claim 9, Line 32: Please delete the ";" at the end of the compound